(12) United States Patent
Kuramochi et al.

(10) Patent No.: US 7,477,177 B2
(45) Date of Patent: Jan. 13, 2009

(54) A-D CONVERTER, A-D CONVERT METHOD, AND A-D CONVERT PROGRAM

(75) Inventors: Yasuhide Kuramochi, Tokyo (JP); Akira Matsuzawa, Tokyo (JP)

(73) Assignees: Advantest Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 11/520,436

(22) Filed: Sep. 13, 2006

(65) Prior Publication Data

US 2008/0143574 A1    Jun. 19, 2008

(51) Int. Cl.
*H03M 1/12*    (2006.01)
(52) U.S. Cl. .................. 341/156; 341/155; 341/158
(58) Field of Classification Search .......... 341/155, 341/156, 158
See application file for complete search history.

(56) References Cited

U.S. PATENT DOCUMENTS

| | | | | |
|---|---|---|---|---|
| 5,455,583 | A * | 10/1995 | Stryjewski | 341/156 |
| 6,281,828 | B1 * | 8/2001 | Kimura et al. | 341/155 |
| 6,340,942 | B1 * | 1/2002 | Zhou et al. | 341/158 |
| 6,674,385 | B2 * | 1/2004 | Micheloni et al. | 341/155 |
| 6,801,150 | B2 | 10/2004 | Honda et al. | |
| 7,187,317 | B2 * | 3/2007 | Oka | 341/156 |
| 2002/0196171 | A1 * | 12/2002 | Micheloni et al. | 341/156 |
| 2003/0174082 | A1 | 9/2003 | Honda | |

FOREIGN PATENT DOCUMENTS

| | | |
|---|---|---|
| JP | 2-104024 | 4/1990 |
| JP | 2104024 | 4/1990 |
| JP | 2278918 | 11/1990 |
| JP | 4255113 | 9/1992 |
| JP | 5-160727 | 6/1993 |
| JP | 5152960 | 6/1993 |
| JP | 2003273735 | 9/2003 |
| WO | 9904496 | 1/1999 |

OTHER PUBLICATIONS

R. E. Suarez, et al., "An All-MOS Charge-Redistribution A/D Conversion Technique", IEEE International Solid-State Circuits Conference, 1974, p. 194-195 and 248.

(Continued)

*Primary Examiner*—Jean B Jeanglaude
(74) *Attorney, Agent, or Firm*—Osha •Liang LLP

(57) ABSTRACT

An A-D converter that outputs a digital output signal obtained by digitalizing an analog input signal includes a plurality of comparators that each compare the analog input signal and an analog threshold value based on designated digital threshold data, a high-order field determining section that narrows down a data value corresponding to a high-order field of a predetermined bit number in the digital output signal based on a plurality of comparison results obtained by supplying threshold data different from one another to the plurality of comparators, a low-order field computing section that computes a plurality of candidate values for a data value corresponding to a low-order field of a predetermined bit number located at a side lower than the high-order field, and a low-order field determining section that determines a data value corresponding to the low-order field based on the plurality of candidate values.

12 Claims, 12 Drawing Sheets

OTHER PUBLICATIONS

J. McCreary, et al., "A High-Speed All-MOS Successive-Approximation Weighted Capacitor A/D Conversion Technique", IEEE International Solid-State Circuits Conference, 1975, p. 38-39 and 211.

J.L. McCreary, et al., "All-MOS Charge Redistribution Analog-to-Digital Conversion Techniques-Part 1", IEEE Journal of Solid-State Circuits, vol. SC-10, No. 6, Dec. 1975, p. 371-379.

Japanese Office Action issued in Application No. 2007-544664 dated Jul. 15, 2008, Translation attached (6 pages).

International Search Report for corresponding PCT Application No. PCT/JP2007/067215, dated Oct. 16, 2007 (with partial English translation), 9 pages.

International Search Report for Corresponding PCT Application No. PCT/JP2007/067629, dated Oct. 9, 2007 (with partial English translation), 7 pages.

* cited by examiner

A-D CONVERTER, A-D CONVERT METHOD, AND A-D CONVERT PROGRAM

BACKGROUND

1. Field of the Invention

The present invention relates to an A-D converter, an A-D convert method, and an A-D convert program. More particularly, the present invention relates to an A-D converter, an A-D convert method, and an A-D convert program for outputting a digital output signal obtained by digitalizing an analog input signal.

2. Related Art

An A-D converter converts an analog signal into a digital signal. The A-D converter is classified into a single bit mode quantizing bits by one bit with one clock and a multiple bit mode quantizing bits by multiple bits with one clock. The A-D converter with a single bit mode includes, for example, a successive comparison A-D converter and a $\Delta\Sigma$ type A-D converter. The successive comparison A-D converter is disclosed in Ricardo E. Suarez, Paul R. Gray, and David A. Hodges, "An All-MOS Charge-Redistribution A/D Conversion Technique", IEEE International Solid-State Circuits Conference, 1974, P. 194-195 and 248, James McCreary and Paul R. Gray, "A High-Speed All-MOS Successive-Approximation Weighted Capacitor A/D Conversion Technique", IEEE International Solid-State Circuits Conference, 1975, P. 38-39 and 211, JAMES L. McCREARY and PAUL R. GRAY, "All-MOS Charge Redistribution Analog-to-Digital Conversion Techniques-Part 1", IEEE JOURNAL OF SOLID-STATE CIRCUITS, VOL. SC-10, NO. 6, DECEMBER 1975, P. 371-379. The A-D converter with a multiple bit mode includes, for example, a flash type A-D converter.

Meanwhile, the A-D converter with a multiple bit mode has a short conversion time compared to the A-D converter with a single bit mode. However, in case of the A-D converter with a multiple bit mode, its circuit scale becomes large when realizing high resolution. On the other hand, the A-D converter with a single bit mode has a small circuit scale compared to the A-D converter with a multiple bit mode. However, in case of the A-D converter with a single bit mode, its conversion time gets longer because bits are converted by one bit when realizing certain resolution.

Furthermore, in case of the A-D converter with a multiple bit mode and the A-D converter with a single bit mode, precision becomes bad because a quantization width becomes narrow and likelihood for noises decreases when realizing high resolution. When an input signal is amplified by an operational amplifier in order to solve this, the A-D converters with a multiple bit mode and a single bit mode have increased power consumption and further their precision is dependent on a characteristic of the operational amplifier.

SUMMARY

Therefore, it is an object of some aspects of the present invention to provide an A-D converter, an A-D convert method, and an A-D convert program that can solve the foregoing problems. The above and other objects can be achieved by combinations described in the independent claims. The dependent claims define further advantageous and exemplary combinations of the present invention.

That is, according to the first aspect of the present invention, there is provided an A-D converter that outputs a digital output signal obtained by digitalizing an analog input signal. The A-D converter includes: a plurality of comparators that each compares the analog input signal and an analog threshold value according to designated digital threshold data; a high-order field determining section that narrows down a data value corresponding to a high-order field of a predetermined bit number in the digital output signal based on a plurality of comparison results obtained by supplying threshold data different from one another to the plurality of comparators; a low-order field computing section that computes a plurality of candidate values for a data value corresponding to a low-order field of a predetermined bit number located at a side lower than the high-order field by means of the plurality of comparators; and a low-order field determining section that determines a data value corresponding to the low-order field based on the plurality of candidate values.

The low-order field computing section may concurrently compute a candidate value for the data value corresponding to the low-order field by means of each of a plurality of groups obtained by dividing the plurality of comparators.

The high-order field determining section may concurrently supply threshold data of which data values corresponding to the high-order field are different from one another to each of the plurality of comparators, perform at least one high-order determination phase in which the data value of the high-order field is narrowed down on a data value between the maximum threshold data by which a comparison result showing that the analog input signal is not less than an analog value according to this threshold data is generated and the minimum threshold data by which a comparison result showing that the analog input signal is less than the analog value according to this threshold data is generated, and determine the data value of the high-order field to one value.

The low-order field computing section may, for each of the plurality of groups obtained by dividing the plurality of comparators by one, set an initial value of the candidate value to a data value determined by the high-order field determining section as a data value for the high-order field and zero as a data value for the low-order field, supply the threshold data in which this bit in the candidate value is one to the comparator in this group sequentially from the most significant bit for each bit from the most significant bit to the least significant bit of the low-order field, update the candidate value by setting this bit of the candidate value to one when the analog input signal is not less than the analog threshold value according to the threshold data and this bit of the candidate value to zero when the analog input signal is less than the analog threshold value, and supply the candidate value obtained by updating the candidate value to the least significant bit of the low-order field to the low-order field determining section.

The low-order field computing section may, for each of the plurality of groups obtained by dividing the plurality of comparators into two or more comparators, concurrently supply threshold data of which data values corresponding to the low-order field are different from one another to each of the plurality of comparators, perform at least one low-order determination phase in which a candidate value of the data value of the low-order field is narrowed down on a data value between the maximum threshold data by which a comparison result showing that the analog input signal is not less than an analog value according to this threshold data is generated and the minimum threshold data by which a comparison result showing that the analog input signal is less than the analog value according to this threshold data is generated, in order to narrow down a data value of the low-order field of the digital output signal, and determine the data value of the low-order field to one value.

The low-order field computing section may perform, for each of the plurality of candidate values, at least one low-order determination phase in which a data value corresponding to the low-order field is narrowed down and determines the data value of the low-order field of this candidate value to one value, based on a plurality of comparison results obtained by supplying threshold data different from one another to the plurality of comparators.

The low-order field determining section may determine a mean value for the plurality of candidate values as the data value of the low-order field.

The low-order field determining section may determine, among the plurality of candidate values, a mean value for at least one candidate value as the data value of the low-order field, the difference between the mean value for at least one candidate value and the mean value for the plurality of candidate values being not more than a predetermined maximum error value.

The A-D converter may further include a sign determining section that supplies the threshold data in which an analog threshold value zero is designated to at least one of the plurality of comparators and determines a sign of the analog input signal in advance of the determination of data values for the high-order field and the low-order field.

According to the second aspect of the present invention, there is provided an A-D convert method for outputting a digital output signal obtained by digitalizing an analog input signal. The A-D convert method includes: a high-order field determining step of narrowing down a data value corresponding to a high-order field of a predetermined bit number in the digital output signal based on a plurality of comparison results obtained by supplying threshold data different from one another to a plurality of comparators that each compares the analog input signal and an analog threshold value according to designated digital threshold data; a low-order field computing step of computing a plurality of candidate values for a data value corresponding to a low-order field of a predetermined bit number located at a side lower than the high-order field by means of the plurality of comparators; and a low-order field determining step of determining a data value corresponding to the low-order field based on the plurality of candidate values.

According to the third aspect of the present invention, there is provided an A-D convert program for computing a digital output signal obtained by digitalizing an analog input signal by means of a computer. The program makes the computer function as: a high-order field determining section that narrows down a data value corresponding to a high-order field of a predetermined bit number in the digital output signal based on a plurality of comparison results obtained by supplying threshold data different from one another to a plurality of comparators that each compares the analog input signal and an analog threshold value according to designated digital threshold data; a low-order field computing section that computes a plurality of candidate values for a data value corresponding to a low-order field of a predetermined bit number located at a side lower than the high-order field by means of the plurality of comparators; and a low-order field determining section that determines a data value corresponding to the low-order field based on the plurality of candidate values.

The summary does not necessarily describe all necessary features of the present invention. The present invention may also be a sub-combination of the features described above.

DESCRIPTION OF EXEMPLARY EMBODIMENTS

The embodiments of the invention will now be described based on the preferred embodiments, which do not intend to limit the scope of the present invention, but just exemplify the invention. All of the features and the combinations thereof described in the embodiment are not necessarily essential to the invention.

Figure 1:
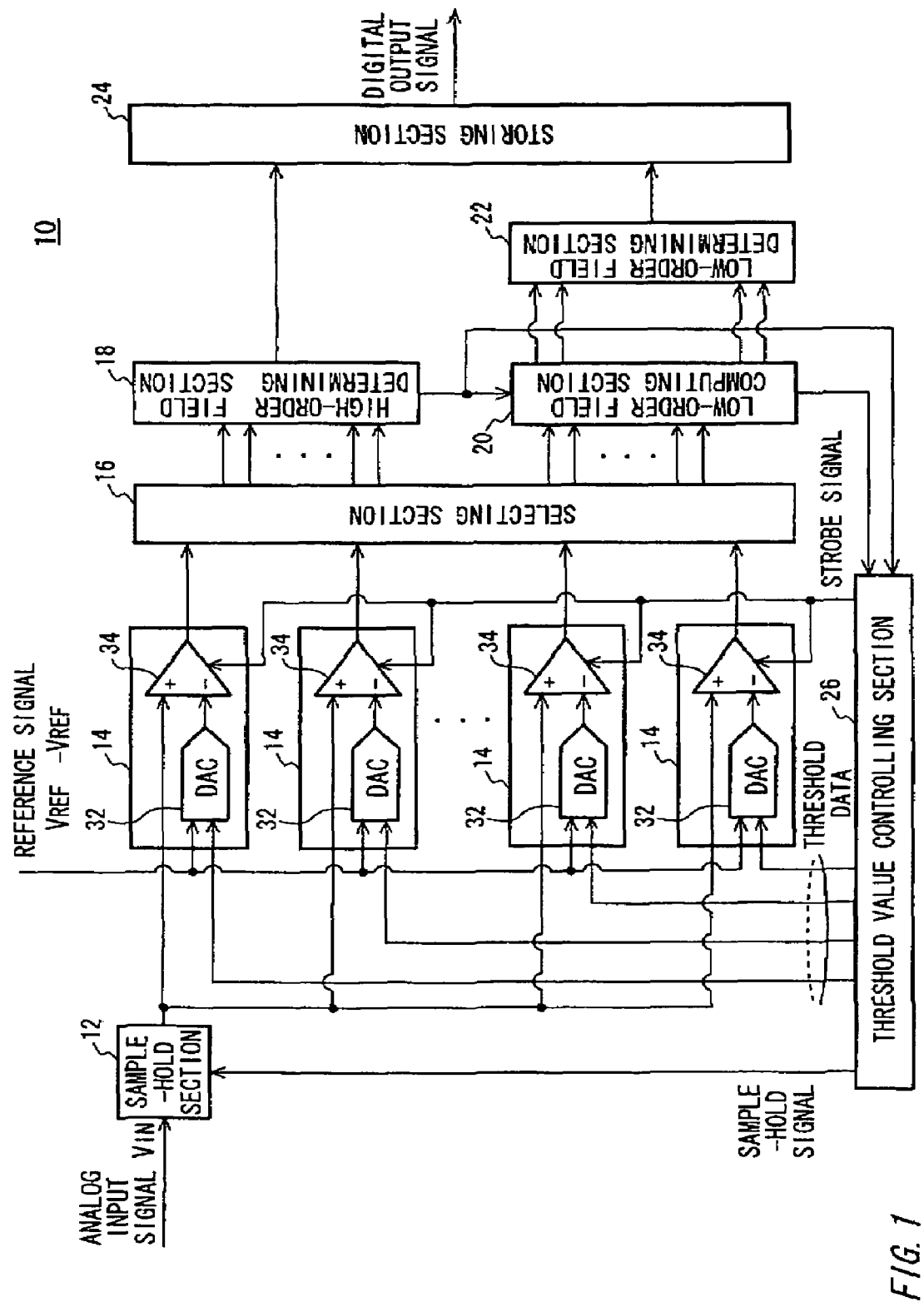
FIG. 1 is a view showing a configuration of an A-D converter according to the present embodiment.

FIG. 1 is a view showing a configuration of an A-D (analog to digital) converter 10 according to the present embodiment. The A-D converter 10 outputs a digital output signal obtained by digitalizing an analog input signal. In the present embodiment, the A-D converter 10 converts a voltage value $V_{IN}$ of the analog input signal into a data value of a predetermined number of bits for each predetermined conversion period.

The A-D converter 10 includes a sample-hold section 12, a plurality of comparators 14, a selecting section 16, a high-order field determining section 18, a low-order field computing section 20, a low-order field determining section 22, a storing section 24, and a threshold value controlling section 26. The sample-hold section 12 samples an analog input signal according to a sample-hold signal, and holds the sampled analog input signal. The sample-hold section 12 may sample, as an example, a voltage value $V_{IN}$ of the analog input signal by means of a capacitor to hold the voltage value $V_{IN}$ of the analog input signal sampled by the capacitor for a certain period.

Each of the plurality of comparators 14 compares the analog input signal held by the sample-hold section 12 and an analog threshold value according to digital threshold data designated by the threshold value controlling section 26. Each of the plurality of comparators 14 may designate, as an example, a threshold voltage by means of threshold data having a bit number (for example, n bits (n is an integer number not less than two)) equal to a data value of a digital output signal, and compare the designated threshold voltage and the voltage value $V_{IN}$ of the analog input signal. In this case, each of the plurality of comparators 14 may have a DAC 32 and a comparing circuit 34 as an example. The DAC 32 outputs one voltage of a plurality of voltages obtained by dividing a voltage interval between a voltage value of a reference signal and a ground by $2^n$ steps of which an interval is substantially equal, according to the designated threshold data. The comparing circuit 34 compares the voltage value $V_{IN}$ of the analog input signal held by the sample-hold section 12 and the threshold voltage output from the DAC 32. In the present embodiment, the comparator 14 outputs Low logic (zero) when there is generated a comparison result showing that the analog input signal is not less than an analog threshold value according to the threshold data, and outputs High logic (one) when there is generated a comparison result showing that the analog input signal is less than the analog threshold value according to the threshold data.

The selecting section 16 supplies the plurality of comparison results output from each of the plurality of comparators 14 to the high-order field determining section 18 and the low-order field computing section 20. The high-order field determining section 18 narrows down a data value corresponding to a high-order field of a predetermined bit number in the digital output signal based on the plurality of comparison results obtained by supplying threshold data different from one another to the plurality of comparators 14.

The low-order field computing section 20 computes a plurality of candidate values of a data value corresponding to a low-order field of a predetermined bit number located at a side lower than the high-order field by means of the plurality of comparators 14. As an example, the low-order field computing section 20 may concurrently compute candidate values for a data value corresponding to a low-order field by means of each of a plurality of groups made by dividing the plurality of comparators 14. The low-order field determining section 22 determines a data value corresponding to the low-order field based on the plurality of candidate values.

The storing section 24 stores data values for a high-order field and a low-order field of digital output signals determined by the high-order field determining section 18 and the low-order field determining section 22. The threshold value controlling section 26 outputs threshold data to be designated for each of the plurality of comparators 14 according to the control of the high-order field determining section 18 and the low-order field computing section 20. Furthermore, the threshold value controlling section 26 outputs a strobe signal designating a comparison timing by the plurality of comparators 14 and a sample-hold signal designating a sample timing and a hold timing of an analog input signal by the sample-hold section 12.

The A-D converter 10 with the above configuration performs a conversion process having two stages within a conversion period for one sample. First, in the first stage, the A-D converter 10 determines a data value corresponding to a high-order field of a predetermined bit number in a digital output signal by means of a multiple-bit conversion process using the plurality of comparators 14. Subsequently, in the second stage, the A-D converter 10 concurrently executes a successive comparison process by multiple times on a data value corresponding to a low-order field of a predetermined bit number located at a side lower than a high-order field in order to compute a plurality of candidate values, and determines one data value based on the plurality of candidate values.

In addition, a high-order field may be relatively located at a bit higher than a low-order field, and is not limited to a field located at a high-order side among bits obtained by dividing all bits of a digital output signal. Similarly, a low-order field may be relatively located at a bit lower than a high-order field, and is not limited to a field located at a low-order side among bits obtained by dividing all bits of a digital output signal.

Figure 2:
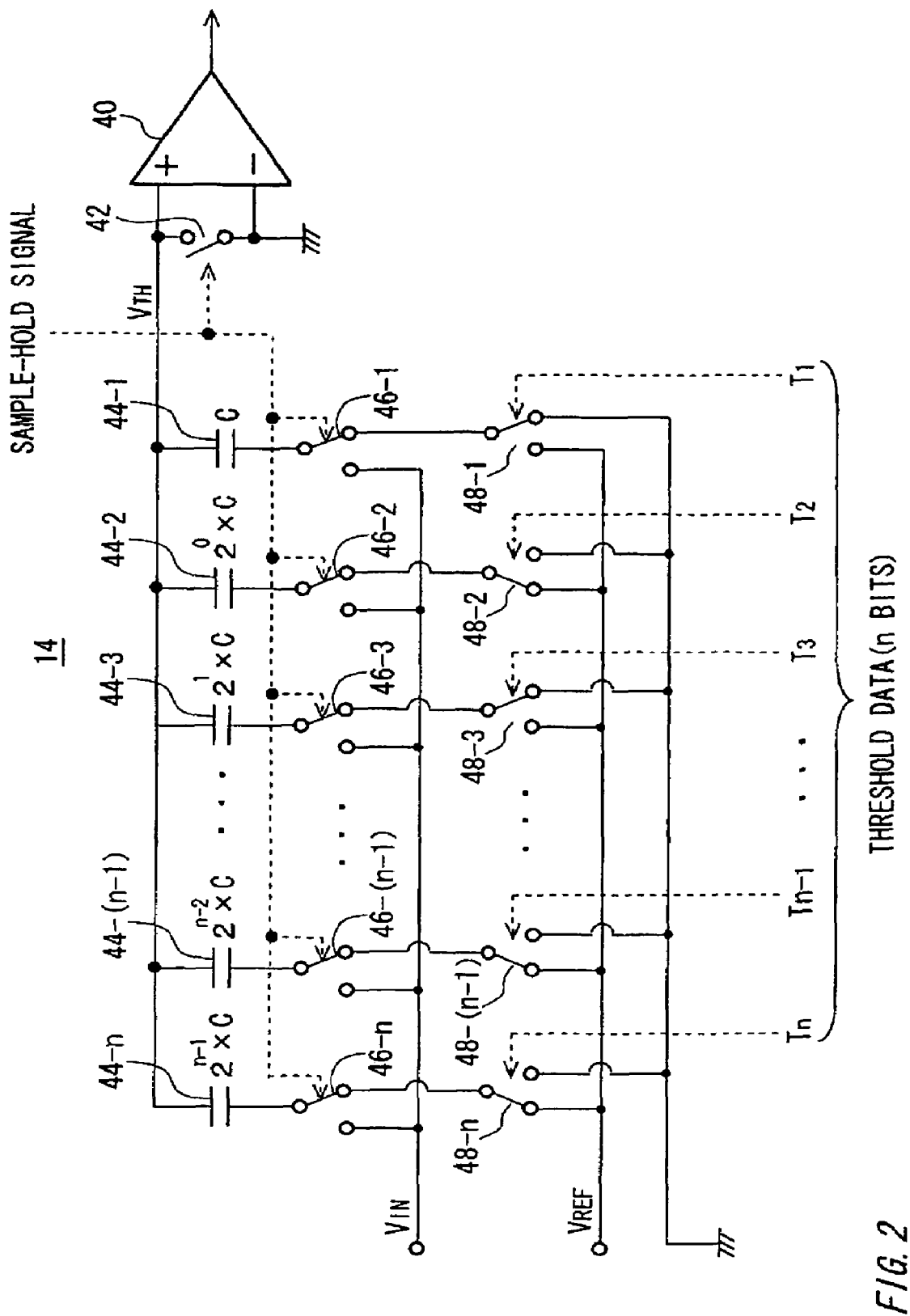
FIG. 2 is a view exemplary showing a configuration of a comparator according to the present embodiment.

FIG. 2 is a view exemplary showing a configuration of a comparator 14 according to the present embodiment. The comparator 14 may have a comparing circuit 40, a sample switch 42, a first to nth capacitors 44-1 to 44-n, a first to nth input change-over switches 46-1 to 46-n, and a first to nth bit switches 48-1 to 48-n as an example. In addition, n is the number of bits for threshold data, and is an integer number not less than two.

In the comparing circuit 40, its minus input terminal is connected t a ground. The comparing circuit 40 outputs High logic (one) when a voltage applied to its plus input terminal is not less than a voltage (ground potential) applied to the minus input terminal and outputs Low logic (zero) when an applied voltage to the plus input terminal is less than the voltage (ground potential) applied to the minus input terminal.

The sample switch 42 connects the plus input terminal of the comparing circuit 40 to a ground when a sample is designated by a sample-hold signal and opens the plus input terminal of the comparing circuit 40 and the ground when a hold is designated by the sample-hold signal.

The first to nth capacitors 44-1 to 44-n correspond to each bit of n-bit threshold data in order. In other words, the first capacitor 44-1 corresponds to the first bit (the least significant bit) from a low-order, the second capacitor 44-2 corresponds to the second bit from the low-order, the third capacitor 44-3 corresponds to the third bit from the low-order, . . . , and then the nth capacitor 44-n corresponds to the nth bit (the most significant bit) from the low-order. A capacity of the first capacitor 44-1 is a predetermined value C, a capacity of the second capacitor 44-2 is $2^0 * C$ that is $2^0$ time (one time) of the predetermined value C, a capacity of the third capacitor 44-3 is $2^1 * C$ that is $2^1$ times of the predetermined value C, a capacity of the fourth capacitor 44-4 is $2^2 * C$ that is $2^2$ times of the predetermined value C, . . . , and then a capacity of the nth capacitor 44-n is $2^{n-1} * C$ that is $2^{n-1}$ times of the predetermined value C. In the first to nth capacitors 44-1 to 44-n, one end thereof is connected to the plus input terminal of the comparing circuit 40.

The first to nth input change-over switches 46-1 to 46-n correspond to each of the first to nth capacitors 44-1 to 44-na. When a sample is designated by a sample-hold signal, the first to nth input change-over switches 46-1 to 46-n apply an analog input signal $V_{IN}$ to terminals (hereinafter, referred to as the other ends of the first to nth capacitors 44-1 to 44-n) of the first to nth capacitors 44-1 to 44-n that are not connected to the plus input terminal of the comparing circuit 40. When a hold is designated by the sample-hold signal, the first to nth input change-over switches 46-1 to 46-n apply a reference signal $V_{REF}$ or ground potential to the other ends of the first to nth capacitors 44-1 to 44-n.

The first to nth bit switches 48-1 to 48-n correspond to each bit of n-bit threshold data in order. In other words, the first bit switch 48-1 corresponds to the first bit (the least significant bit) from a low-order, the second bit switch 48-2 corresponds to the second bit from the low-order, the third bit switch 48-3 corresponds to the third bit from the low-order, ..., and then the nth bit switch 48-n corresponds to the nth bit (the most significant bit) from the low-order. When a corresponding bit of threshold data is High logic (one), each of the first to nth bit switches 48-1 to 48-n applies the reference signal $V_{REF}$ to the other ends of the corresponding first to nth capacitors 44-1 to 44-n. When a corresponding bit of threshold data is Low logic (zero), each of the first to nth bit switches 48-1 to 48-n applies the ground potential to the other ends of the corresponding first to nth capacitors 44-1 to 44-n.

In the comparator 14 with such a configuration, during sampling, one-side ends of the first to nth capacitors 44-1 to 44-n are connected to a ground and the other ends are applied with the voltage value $V_{IN}$ of the analog input signal. Therefore, the first to nth capacitors 44-1 to 44-n can sample the voltage value $V_{IN}$ of the analog input signal during sampling.

Moreover, in the comparator 14 with such a configuration, during holding, the connection between one-side ends of the first to nth capacitors 44-1 to 44-n and a ground is open, and the application of the voltage value $V_{IN}$ of the analog input signal to the other ends is also stopped. Therefore, the first to nth capacitors 44-1 to 44-n apply a backward voltage ($-V_{IN}$) for the voltage $V_{IN}$ of the held analog input signal to the plus input terminal of the comparing circuit 40 during holding.

Additionally, during holding, in each of the first to nth capacitors 44-1 to 44-n, the voltage $V_{REF}$ is applied to the other end when a corresponding bit value of threshold data is High logic (one) and ground potential is applied to the other end when the corresponding bit value of threshold data is Low logic (zero). Therefore, during holding, each of the first to nth capacitors 44-1 to 44-n can apply a voltage $V_{TH}$ shown in the following Expression (1) to the plus input terminal of the comparing circuit 40.

$$V_{TH} = -V_{IN} + \{(V_{REF}/2^1) \times (T_n) + (V_{REF}/2^2) \times (T_{n-1}) + \ldots + (V_{REF}/2^{n-1}) \times (T_2) + (V_{REF}/2^n) \times (T_1)\} \quad (1)$$

In Expression (1), $T_1$ shows a logical value of the first bit (the least significant bit) from a low-order of threshold data, $T_2$ shows a logical value of the second bit from the low-order of threshold data, ..., and $T_n$ shows a logical value of the nth bit (the most significant bit) from the low-order of threshold data.

The voltage $V_{TH}$ shown in Expression (1) becomes more than ground potential (0V) when the voltage value $V_{IN}$ of the analog input signal is not less than a threshold voltage (a voltage expressed by Expression surrounded with braces { } in Expression (1)) according to the threshold data. Moreover, the voltage $V_{TH}$ becomes less than ground potential (0V) when the voltage value $V_{IN}$ of the analog input signal is less than the threshold voltage according to threshold data.

Then, the comparing circuit 40 outputs a logical value showing a comparison result between the ground potential and the voltage $V_{TH}$. In other words, the comparing circuit 40 outputs Low logic (zero) when the voltage $V_{TH}$ of Expression (1) is not less than ground potential and outputs High logic (one) when the voltage $V_{TH}$ of Expression (1) is less than the ground potential.

According to the comparator 14 with such a configuration, it is possible to compare the voltage value $V_{IN}$ of the analog input signal and the voltage value according to threshold data. Furthermore, according to the comparator 14 with such a configuration, it is possible to have a sample-hold function of the voltage value $V_{IN}$ of the analog input signal. In this way, since the A-D converter 10 does not include the sample-hold section 12, its configuration becomes simple.

Furthermore, in the comparator 14 with such a configuration, when sampling is performed with a capacity equal to that of the comparator including the sample-hold section 12, a sampling time can be shortened because a capacity of the individual capacitor 44 becomes small and thus a time constant is reduced. Moreover, in the comparator 14 with such a configuration, when the individual capacitor 44 samples an analog input signal with precision equal to that of the sample-hold section 12, precision can become well because noises included in the plurality of capacitors 44 are averaged.

Figure 3:
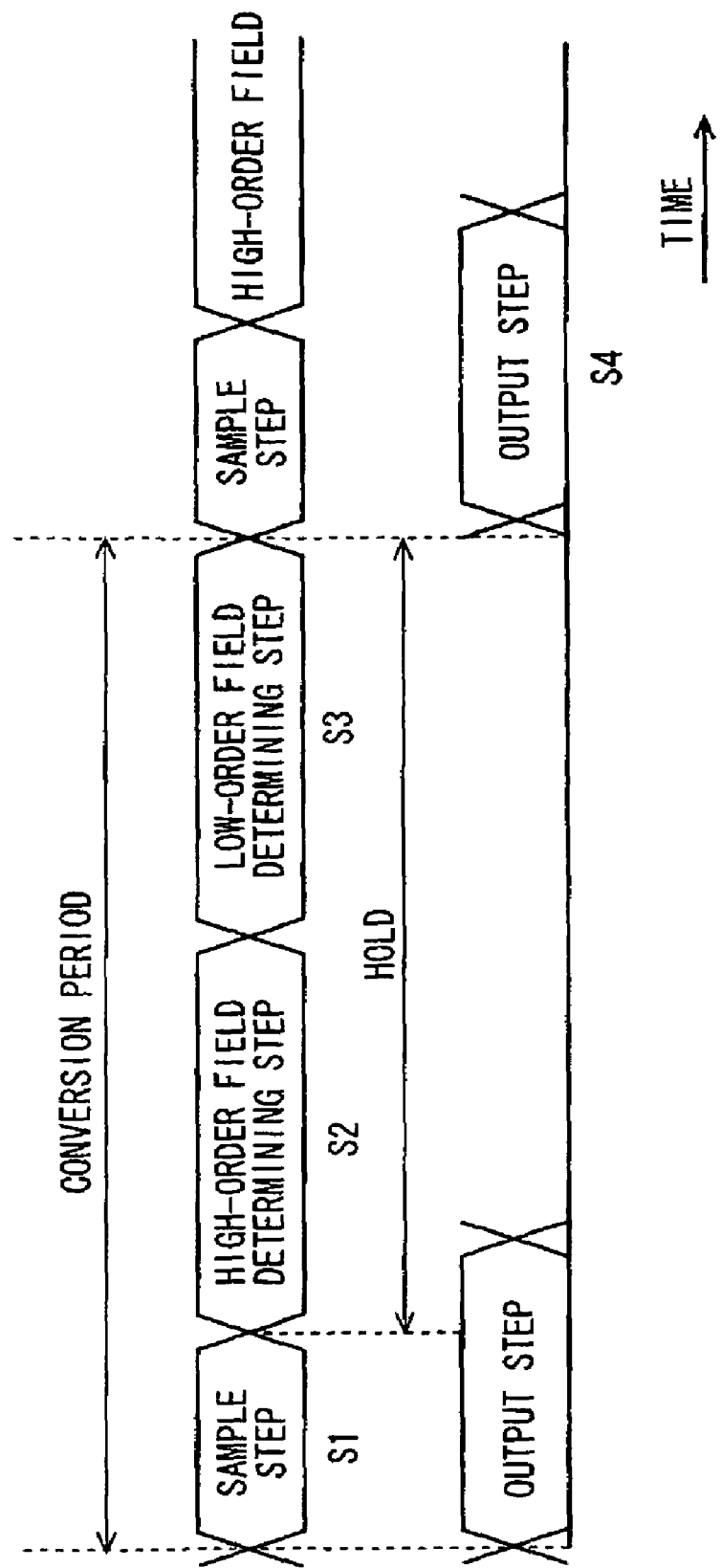
FIG. 3 is a view showing each phase in an analog to digital process by an A-D converter according to the present embodiment.

FIG. 3 is a view showing each phase in an analog to digital process by an A-D converter 10 according to the present embodiment. First, the A-D converter 10 samples an analog input signal in a sample step (S1). The A-D converter 10 holds the sampled analog input signal until a high-order field determining step (S2) and a low-order field determining step (S3) are completed after completing sampling.

Next, in the high-order field determining step (S2), the A-D converter 10 determines a data value corresponding to a high-order field of a digital output signal by at least one time performing a determination phase (a high-order determination phase) of a data value by a multiple-bit conversion process using the plurality of comparators 14. Next, in the low-order field determining step (S3), the A-D converter 10 computes a plurality of candidate values by concurrently executing a successive comparison process on a data value corresponding to a low-order field of the digital output signal by multiple times, and determines one data value based on the plurality of candidate values. Next, in an output step (S4), the A-D converter 10 outputs a data value for all fields of the digital output signal determined in the high-order field determining step (S2) and the low-order field determining step (S3).

The A-D converter 10 repeats the above S1 to S4 steps for each conversion period. In this way, the A-D converter 10 can output a data value obtained by converting an analog input signal into a digital value for each conversion period. In addition, the A-D converter 10 may perform the output step (S4) outputting a data value converted in this conversion period after this conversion period when the sample step (S1), the high-order field determining step (S2), and the low-order field determining step (S3) are performed within one conversion period.

Figure 4:
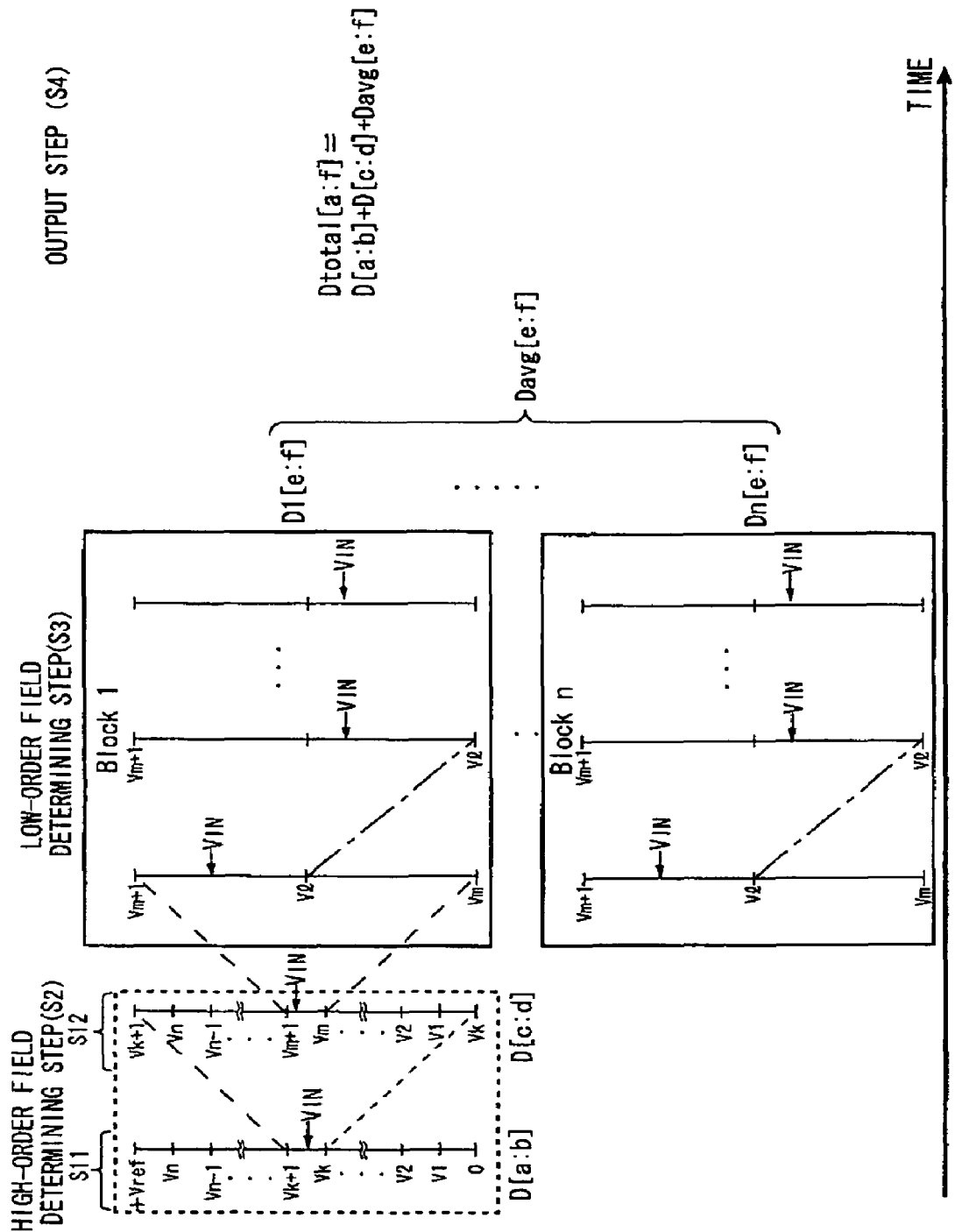
FIG. 4 is a view exemplary showing a conversion process by an A-D converter when a plurality of comparators performs a multiple-bit conversion process in a high-order field determining step (S2) and each of the plurality of comparators performs a successive comparison process in a low-order field determining step (S3).

FIG. 4 is a view exemplary showing a conversion process by an A-D converter 10 when a plurality of comparators 14 performs a multiple-bit conversion process in a high-order field determining step (S2) and each of the plurality of comparators 14 performs a successive comparison process in a low-order field determining step (S3).

In addition, as an example, FIG. 4 shows the case when a<b<c<d<e<f (a to f are an integer number not less than one), a data value (D[a:b]) of the ath and bth bits from a high-order in a digital output signal and a data value (D[c:d]) of the cth and dth bits from the high-order are respectively determined in the high-order field determining step (S2), and a data value (Davg [e:f]) of the eth and fth bits from the high-order in the digital output signal is determined in the low-order field determining step (S3). Moreover, in this case, the number of bits of threshold data is a bit number equal to that of a digital output signal. Moreover, in FIG. 4, a dotted line linking scale showing a threshold value in S11 and scale showing a threshold value in S12 is an equivalent threshold value. In FIG. 4, a dotted line between S12 and S3 is also similar.

In the high-order field determining step (S2), as an example, the high-order field determining section 18 may perform a determination phase (a high-order determination phase) of a data value by a multiple-bit conversion process using the plurality of comparators 14 by multiple times, in order to determine a data value corresponding to a high-order field of a digital output signal. As an example, as shown in FIG. 4, the high-order field determining section 18 may determine a data value (D[a:b]) of the ath and bth bits by a first high-order determination phase (S11) and then determine a data value (D[c:d]) of the cth and dth bits by a second high-order determination phase (S12).

In the first high-order determination phase (S11), the high-order field determining section 18 controls the threshold value controlling section 26 in order to concurrently supply threshold data, in which data values corresponding to a high-order field are different from each other, to each of the plurality of comparators 14. As an example, in the first high-order determination phase (S11), the high-order field determining section 18 may concurrently supply threshold data, in which data values of the ath and bth bits are different from each other and the other bits are equal to one another, to each of the plurality of comparators 14. The high-order field determining section 18 may concurrently supply, as an example, threshold data different from one another to each of the plurality of comparators 14, in order to generate $2^{(b-a+1)}$ threshold voltages obtained by substantially equally dividing a range, e.g., not less than 0V and not more than $+V_{REF}$ into $2^{(b-a+1)}$ stages in each of the plurality of comparators 14.

In the first high-order determination phase (S11), each of the plurality of comparators 14 supplied with threshold data compares whether an analog input signal is not less than an analog value according to the corresponding threshold data. The high-order field determining section 18 narrows down a data value of a high-order field to a data value between the maximum threshold data by which a comparison result showing that the analog input signal is not less than an analog value according to this threshold data is generated and the minimum threshold data by which a comparison result showing that the analog input signal is less than the analog value according to this threshold data is generated, based on comparison results by the plurality of comparators 14. The high-order field determining section 18 may determine a data value of a high-order field in a digital output signal to a value of a high-order field in the maximum threshold data by which a comparison result showing that the analog input signal is not less than an analog value according to this threshold data is generated, as an example. In the present example, the high-order field determining section 18 may determine a data value of the ath and bth bits in a digital output signal to a data value of the ath and bth bits of the maximum threshold data by which a comparison result showing that the analog input signal is not less than an analog value according to this threshold data is generated.

Next, in the second high-order determination phase (S12), the high-order field determining section 18 controls the threshold value controlling section 26 in order to concurrently supply threshold data, in which data values corresponding to a high-order field to be determined in this phase are different from one another and the other bits are equal to one other, to each of the plurality of comparators 14. In this case, the high-order field determining section 18 supplies threshold data in which a field value of which a data value up to the preceding phase is determined is set to this determined data value. As an example, the high-order field determining section 18 may concurrently supply threshold data, in which the ath and bth bits are set to data values determined in the first high-order determination phase (S11), the cth and dth bits are set to data values different from each other, and the eth and fth bits are set to the same data value (for example, zero), to each of the plurality of comparators 14.

As an example, the high-order field determining section 18 may concurrently supply threshold data different from one another to each of the plurality of comparators 14, in order to generate $2^{(d-c+1)}$ threshold voltages obtained by substantially equally dividing, into $2^{(d-c+1)}$ stages, a range not less than a threshold voltage corresponding to the maximum threshold data by which a comparison result showing that the analog input signal is not less than an analog value according to this threshold data is generated in the preceding phase and not more than a threshold voltage corresponding to the minimum threshold data by which a comparison result showing that the analog input signal is less than the analog value according to this threshold data is generated in the preceding phase.

In the second high-order determination phase (S12), each of the plurality of comparators 14 supplied with threshold data compares whether the analog input signal is not less than an analog value according to the corresponding threshold data. The high-order field determining section 18 narrows down a data value of the high-order field to be determined in this phase to a data value between the maximum threshold data by which a comparison result showing that the analog input signal is not less than an analog value according to this threshold data is generated and the minimum threshold data by which a comparison result showing that the analog input signal is less than the analog value according to this threshold data is generated, based on comparison results by the plurality of comparators 14. As an example, the high-order field determining section 18 may determine a data value of a high-order field in a digital output signal to a value of a high-order field in the maximum threshold data by which a comparison result showing that the analog input signal is not less than an analog value according to this threshold data is generated. In the present example, the high-order field determining section 18 may determine a data value of the cth and dth bits in a digital output signal to a data value of the cth and dth bits of the maximum threshold data by which a comparison result showing that the analog input signal is not less than an analog value according to this threshold data is generated.

As described above, in the high-order field determining step (S2), the high-order field determining section 18 performs at least one determination phase for a data value by a multiple-bit conversion process (a high-order determination phase), and determines a data value corresponding to the high-order field to one value.

In addition, in the multiple-bit conversion process, the high-order field determining section 18 may change correspondence between the plurality of threshold data to be generated and the plurality of comparators 14 supplied with the plurality of threshold data, for example, for each conversion period. As an example, the high-order field determining section 18 may change correspondence between the plurality of threshold data and the plurality of comparators 14 according to a random number. In this way, according to the A-D converter 10, it is possible to reduce noises because fluctuation of precision between the plurality of comparators 14 is averaged.

After the high-order field determining step (S2) is completed, the low-order field computing section 20 and the low-order field determining section 22 compute a plurality of candidate values by concurrently executing a successive comparison process on a data value corresponding to a low-order field of a digital output signal by multiple times, and determine one data value based on the plurality of candidate values, in the low-order field determining step (S3).

In the low-order field determining step (S3), the low-order field computing section 20 controls the threshold value controlling section 26 in order to compute a plurality of candidate values for a data value corresponding to a low-order field by a successive comparison process using the plurality of comparators 14 for each of the plurality of groups made by dividing the plurality of comparators 14 by one. In other words, the low-order field computing section 20 makes each of the plurality of comparators 14 operate in correspondence with a successive comparison process to concurrently compute values corresponding to the low-order field. In this way, the low-order field computing section 20 can obtain the plurality of candidate values computed by the successive comparison process. In the present example, the low-order field computing section 20 may make each of the plurality of comparators 14 operate in correspondence with the successive comparison process to compute the plurality of candidate values of the eth and fth bits.

Then, the low-order field determining section 22 determines a data value corresponding to a low-order field based on the plurality of candidate values computed by the low-order field computing section 20. The low-order field determining section 22 may determine a mean value for the plurality of candidate values as a data value of a low-order field as an example. In addition, as an example, the low-order field determining section 22 may determine a mean value for at least one candidate value as the data value of the low-order field, in which the difference between the mean value for at least one candidate value and the mean value for the plurality of candidate values is not more than a predetermined maximum error value. In this way, according to the low-order field determining section 22, it is possible to perform analog to digital conversion with high precision. Moreover, the low-order field determining section 22 may determine a value after the decimal point of a mean value for the plurality of candidate values as a data value lower than this low-order field in the digital output signal.

The low-order field computing section 20 may perform a successive comparison process as follows by means of the comparator 14 as an example.

First, the low-order field computing section 20 sets a data value determined by the high-order field determining section 18 in the high-order field determining step (S2) to a data value of a high-order field and sets an initial value of a candidate value in which zero is a data value of a low-order field as threshold data. In addition, alternatively, the low-order field computing section 20 may set a data value determined by the high-order field determining section 18 to a data value of a high-order field and set an initial value of a candidate value in which one is a data value of a low-order field as threshold data.

Subsequently, the low-order field computing section 20 supplies threshold data in which this bit in a candidate value is one to the comparator 14 in this group, in sequence from the most significant bit for each bit from the most significant bit to the least significant bit of the low-order field. In other words, the low-order field computing section 20 compares an analog input signal and an analog value according to the supplied threshold data for each of the plurality of comparators 14 while concurrently supplying a candidate value, in which bits become one in sequence from the most significant bit between the most significant bit and the least significant bit in a low-order field from a state of an initial value, to each of the plurality of comparators 14 as threshold data.

Alternatively, when setting an initial value of a candidate value in which one is a data value of a low-order field, the low-order field computing section 20 may supply threshold data, in which this bit in a candidate value is zero in sequence from the most significant bit, to the comparator 14 in this group for each bit from the most significant bit to the least significant bit of the low-order field. In other words, the low-order field computing section 20 may compare an analog input signal and an analog value according to the supplied threshold data for each of the plurality of comparators 14 while concurrently supplying a candidate value, in which bits become zero in sequence from the most significant bit between the most significant bit and the least significant bit in a low-order field from a state of an initial value, to each of the plurality of comparators 14 as threshold data.

Furthermore, the low-order field computing section 20 sets this bit of a candidate value to one when an analog input signal is not less than the analog threshold value according to the threshold data and sets this bit to zero when the analog input signal is less than the analog threshold value based on a comparison result by the comparator 14 for each bit from the most significant bit to the least significant bit of the low-order field, and then updates the candidate value. In other words, the low-order field computing section 20 updates a bit of a candidate value that becomes one in this timing to one when an analog input signal is not less than an analog threshold value according to threshold data and updates the bit of the candidate value that becomes one in this timing to zero when the analog input signal is less than the analog threshold value according to threshold data, at each timing at which bits are one in sequence from the most significant bit of the low-order field for each of the plurality of comparators 14.

Alternatively, when setting an initial value of the candidate value in which one is a data value of the low-order field, the low-order field computing section 20 sets this bit of the candidate value to one when an analog input signal is larger than an analog threshold value according to threshold data and sets this bit of the candidate value to zero when the analog input signal is not more than the analog threshold value, and then updates the candidate value. In other words, the low-order field computing section 20 may update a bit of a candidate value that becomes zero in this timing to one when an analog input signal is larger than an analog threshold value according to threshold data and update the bit of the candidate value that becomes zero in this timing to zero when the analog input signal is not more than the analog threshold value according to threshold data, at each timing at which bits are zero in sequence from the most significant bit of the low-order field for each of the plurality of comparators 14.

As described above, since the low-order field computing section 20 sequentially changes a candidate value while the candidate value becomes one from a high-order bit from a state of an initial value (all bits are zero) and sequentially updates bit values in which the candidate value becomes one according to the comparison result, the low-order field computing section 20 can gradually perform analog to digital conversion every one bit from the high-order bit.

Subsequently, the low-order field computing section 20 supplies a candidate value obtained by updating the candidate value to the least significant bit of the low-order field to the low-order field determining section 22. As described above, in the low-order field determining step (S3), the low-order field computing section 20 can determine a plurality of candidate values corresponding to a low-order field by a parallel successive comparison process.

In addition, the low-order field computing section 20 may further perform the parallel successive comparison process by multiple times in a time direction as an example. In other words, the low-order field computing section 20 may perform a process for computing a plurality of candidate values by a successive comparison process by m times (m is an integer number not less than one). Then, the low-order field determining section 22 may determine a data value corresponding to a low-order field based on the plurality of candidate values computed by the low-order field computing section 20. The low-order field determining section 22 may determine a mean value for the plurality of candidate values as a data value of a low-order field as an example.

Figure 5:
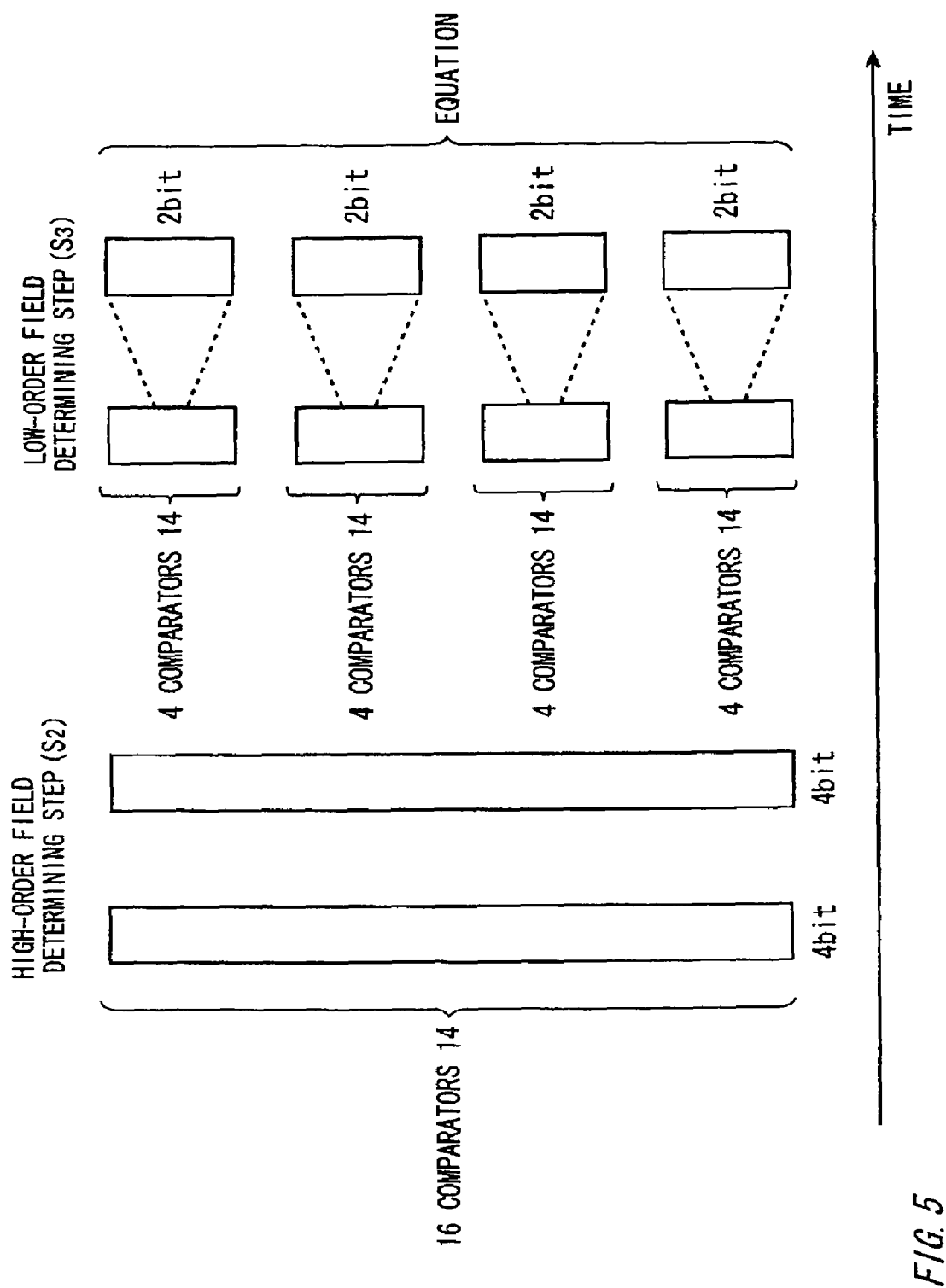
FIG. 5 is a view showing an alternative example in a low-order field determining step (S3).

FIG. 5 is a view showing an alternative example in a low-order field determining step (S3). In the low-order field determining step (S3), the low-order field computing section 20 may execute a process made by combining multiple-bit conversion and a successive comparison process on a plurality of groups obtained by dividing the plurality of comparators 14 into two or more as shown in FIG. 5, in place of the process shown in FIG. 4. For example, the low-order field computing section 20 may divide 16 comparators 14 into groups each having two comparators in order to execute a process made by combining multiple-bit conversion and a successive comparison process on every group including four comparators 14.

In other words, the low-order field computing section 20 performs a process made by combining multiple-bit conversion and a successive comparison process as follows.

The low-order field computing section 20 concurrently supplies threshold data, in which data values corresponding to a low-order field are different from one another, to each of the plurality of comparators 14, for each of the plurality of groups. Each of the plurality of comparators 14 within each group supplied with the threshold data compares whether an analog input signal is not less than an analog value according to the corresponding threshold data.

The low-order field computing section 20 performs at least one low-order determination phase for narrowing down a candidate value for a data value of a low-order field to a data value between the maximum threshold data by which a comparison result showing that the analog input signal is not less than an analog value according to this threshold data is generated and the minimum threshold data by which a comparison result showing that the analog input signal is less than the analog value according to this threshold data is generated, for each group based on the comparison results by each of the plurality of comparators 14 of each group. For example, the low-order field computing section 20 may generate a four-bit candidate value by repeating a low-order determination phase for narrowing down an analog input signal to a two-bit value two times by means of the four comparators 14.

By performing such a process, the low-order field computing section 20 can compute a plurality of candidate values for a data value corresponding to a low-order field for each of the plurality of groups obtained by dividing the plurality of comparators 14 into comparators not less than two.

Moreover, the low-order field computing section 20 may acquire the plurality of candidate values, for example, by continuously performing a multiple-bit conversion process using all the plurality of comparators 14 similar to the process performed in the high-order field determining step by multiple times, in place of the process shown in FIG. 4. In other words, the low-order field computing section 20 may perform a low-order determination phase for computing one candidate value based on the plurality of comparison results obtained by supplying threshold data different from one another to the plurality of comparators 14 by multiple times in a time direction, in order to generate the plurality of candidate values.

Furthermore, for each of the plurality of candidate values, the low-order field computing section 20 may perform at least one low-order determination phase for narrowing down a data value corresponding to a low-order field based on the plurality of comparison results obtained by supplying threshold data different from one another to the plurality of comparators 14, in order to determine a data value of a low-order field of a candidate value to one value. As an example, the low-order field computing section 20 further divides a bit field within a low-order field into a high-order and a low-order, and performs a multiple-bit conversion process making use of all the plurality of comparators 14 on each of the high-order and the low-order. Then, the low-order field computing section 20 may perform this process by multiple times in a time direction to compute the plurality of candidate values.

FIGS. 6 to 9 are views exemplary showing a conversion process when a ten-bit digital output signal is output by performing a high-order determination phase (conversion by a four-bit multiple-bit conversion process) by two times in the high-order field determining step (S2) and performing conversion by a two-bit successive comparison process by multiple times in the low-order field determining step (S3). In addition, in the present example, the A-D converter 10 includes 16 comparators 14 having the DAC 32 and the comparing circuit 34.

Figure 6:
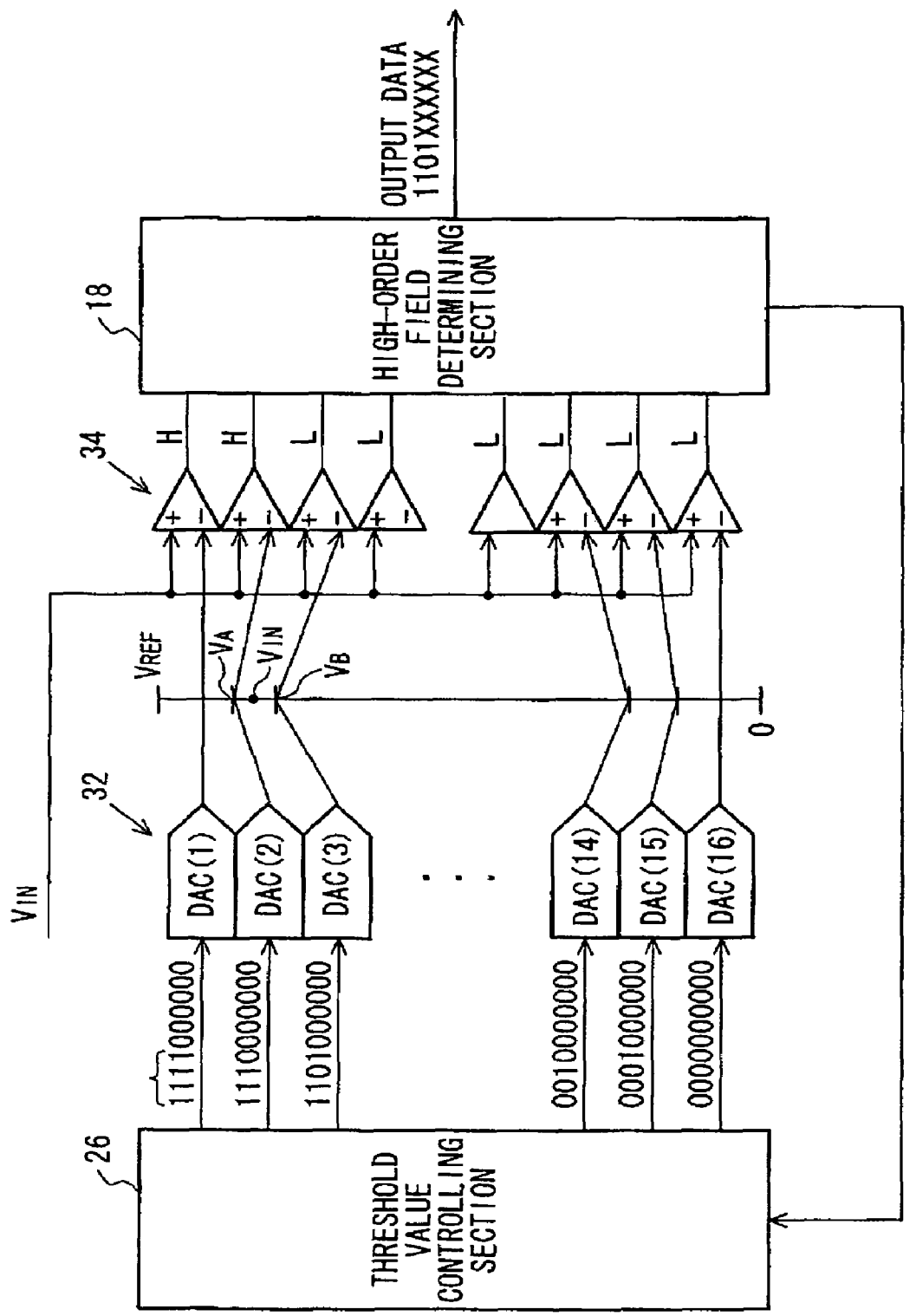
FIG. 6 is a view showing an example in which four bits from the first high-order bit to the fourth high-order bit are converted by a multiple-bit conversion process in a high-order field determining step (a first high-order determination phase).

FIG. 6 is a view showing an example in which four bits from the first high-order bit to the fourth high-order bit are converted by a multiple-bit conversion process in the high-order field determining step (the first high-order determination phase). In the first high-order determination phase of the high-order field determining step, the high-order field determining section 18 sets bits from the first high-order bit to the fourth high-order bit to each values from 0000 to 1111, and supplies each of 16 threshold data of which bits from the fifth high-order bit to the tenth high-order bit are set to zero to the corresponding DAC 32. In this way, the high-order field determining section 18 can generate a threshold voltage in each step obtained by dividing a voltage between 0V and $V_{REF}$ into 16 steps by means of the 16 DACs 32.

The 16 comparing circuits 34 compares a threshold voltage and a voltage value $V_{IN}$ of an analog input signal, and each outputs a comparison result. As a result, the 16 comparing circuits 34 in the selecting section output Low logic (zero) when the voltage value $V_{IN}$ of the analog input signal is not less than a threshold voltage and output High logic (one) when the voltage value $V_{IN}$ of the analog input signal is less than the threshold voltage. The high-order field determining section 18 determines a data value from the first high-order bit to the fourth high-order bit in the maximum threshold data, in which a comparison result (Low logic (zero)) showing that the analog input signal is not less than an analog value according to threshold data is generated, as a data value from the first high-order bit to the fourth high-order bit of an output value. In the present example, the high-order field determining section 18 determines 1101 as a data value from the first high-order bit to the fourth high-order bit.

Figure 7:
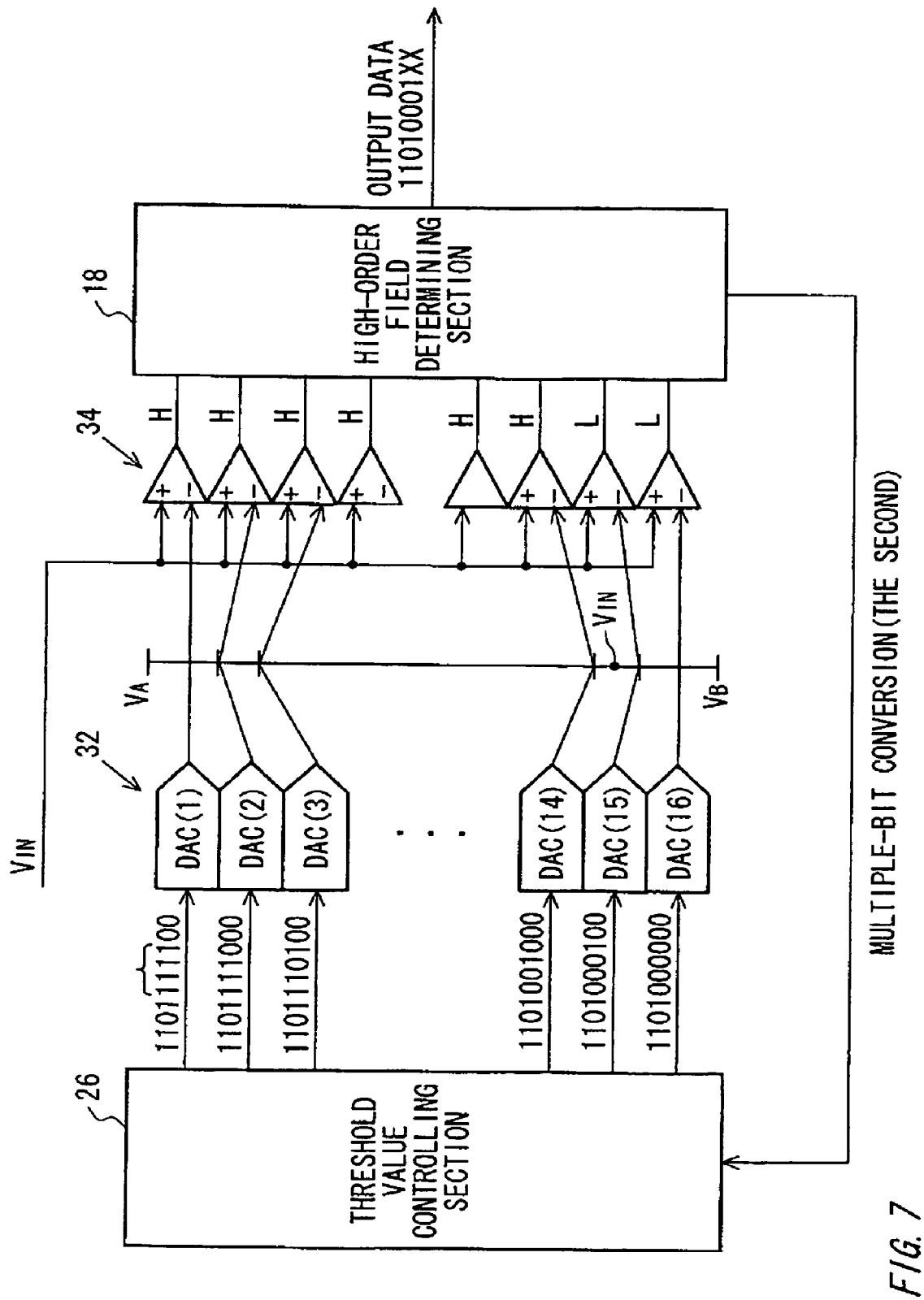
FIG. 7 is a view showing an example in which four bits from the fifth high-order bit to the eighth high-order bit are converted by a multiple-bit conversion process in a high-order field determining step (a second high-order determination phase).

FIG. 7 is a view showing an example in which four bits from the fifth high-order bit to the eighth high-order bit are converted by a multiple-bit conversion process in the high-order field determining step (the second high-order determination phase). In the second high-order determination phase of the high-order field determining step, the high-order field determining section 18 sets bits from the first high-order bit to the fourth high-order bit the data value (1101 in the present example) determined in the preceding phase, sets bits from the fifth high-order bit to the eighth high-order bit to each value from 0000 to 1111, and supplies each of 16 threshold data in which bits from the ninth high-order bit to the tenth high-order bit are set to zero to the corresponding DAC 32.

In this way, the high-order field determining section 18 can generate a threshold voltage of each phase obtained by dividing, into 16 steps, a range between a threshold voltage corresponding to the maximum threshold data in which a comparison result showing that an analog input signal is not less than an analog value according to threshold data is generated in the preceding phase and a threshold voltage corresponding to the minimum threshold data in which a comparison result showing that an analog input signal is less than an analog value according to threshold data is generated in the preceding phase, by means of the 16 DACs 32.

The 16 comparing circuits 34 compare a threshold voltage and a voltage value $V_{IN}$ of an analog input signal, and each outputs a comparison result. The high-order field determining section 18 determines a data value from the fifth high-order bit to the eighth high-order bit in the maximum threshold data, in which a comparison result (Low logic (zero)) showing that an analog input signal is not less than an analog value according to threshold data is generated, as a data value from the fifth high-order bit to the eighth high-order bit of the output value. In the present example, the high-order field determining section 18 determines 0001 as a data value from the fifth high-order bit to the eighth high-order bit.

Figure 8:
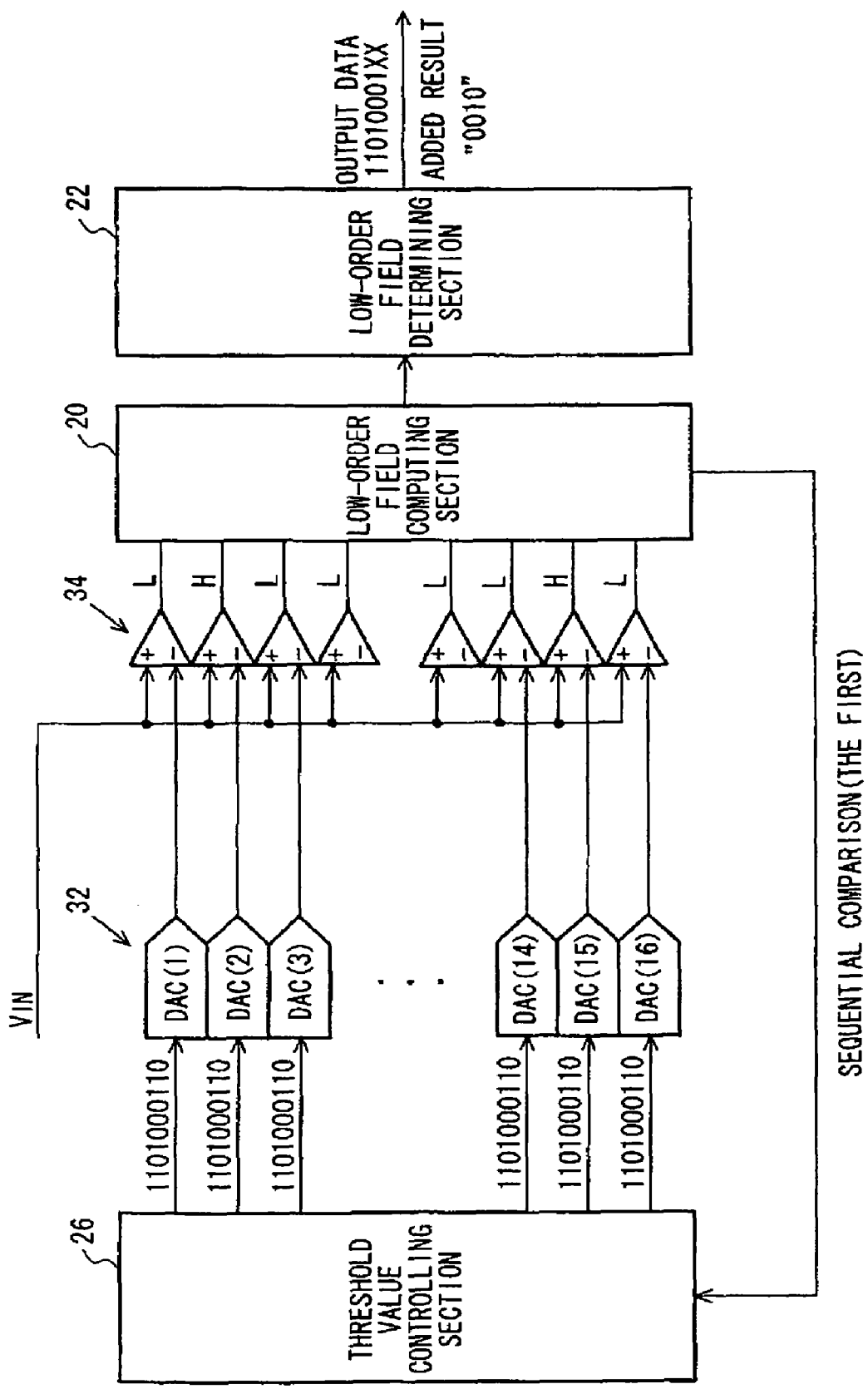
FIG. 8 is a view showing an example in which one bit of the ninth high-order bit is concurrently converted by a successive comparison process by multiple times in a low-order field determining step.

FIG. 8 is a view showing an example in which one bit of the ninth high-order bit is concurrently converted by a successive comparison process by multiple times in the low-order field determining step. In the low-order field determining step, the low-order field computing section 20 sets bits from the first high-order bit to the eighth high-order bit to the data value (in the present example, 11010001) determined in the high-order field determining step, sets the ninth high-order bit to one, and supplies threshold data of which the tenth high-order bit is set to zero to each of the 16 DACs 32.

In this way, the low-order field computing section 20 can respectively generate, from the 16 DACs 32, a boundary voltage when dividing, by two, a range between a threshold voltage corresponding to the maximum threshold data in which a comparison result showing that an analog input signal is not less than an analog value according to threshold data is generated in the high-order field determining step and a threshold voltage corresponding to the minimum threshold data in which a comparison result showing that the analog input signal is less than the analog value according to threshold data is generated in the high-order field determining step.

The 16 comparing circuits 34 compare a threshold voltage and a voltage value $V_{IN}$ of the analog input signal, and each outputs a comparison result (i.e., a candidate value for the ninth bit). Here, the 16 comparing circuits 34 generate comparison results with fluctuation because noises are included during conversion, even if the same comparison result should be ideally output. In the present example, 14 circuits of the 16 comparing circuits 34 output a comparison result (Low logic (zero)) showing that the analog input signal is not less than the analog value according to threshold data, and two circuits of the 16 comparing circuits 34 output a comparison result (High logic (one)) showing that the analog input signal is less than the analog value according to threshold data.

The low-order field determining section 22 adds the comparison results (i.e., candidate values for the ninth bit) output from the 16 comparing circuits 34. In the present example, the low-order field determining section 22 can obtain 0010 as an added result because 14 Low logic (zero) and two High logic (one) are added.

Figure 9:
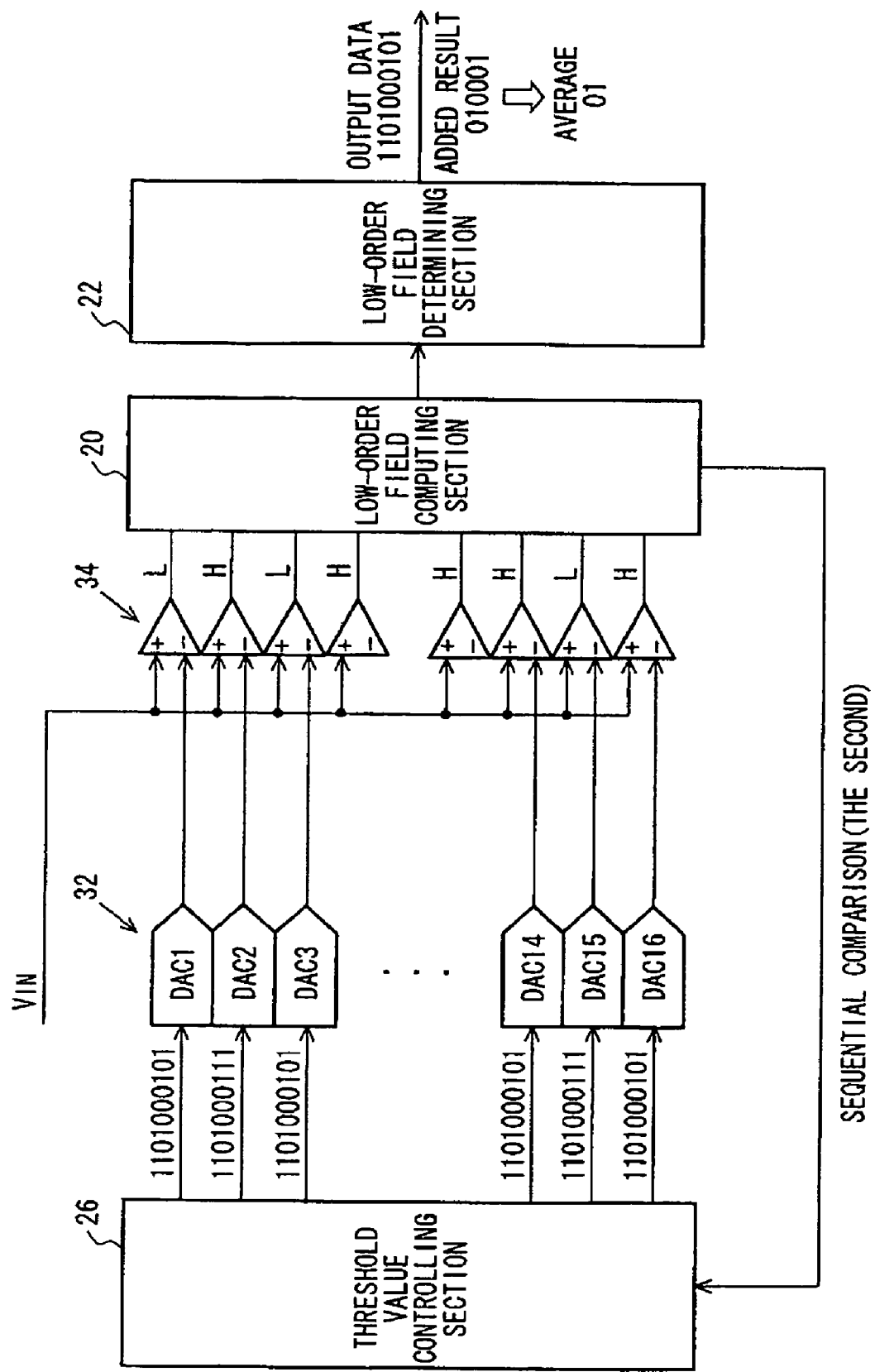
FIG. 9 is a view showing an example in which one bit of the tenth high-order bit (least significant bit) is concurrently converted by a successive comparison process by multiple times in a low-order field determining step.

FIG. 9 is a view showing an example in which one bit of the tenth high-order bit (least significant bit) is concurrently converted by a successive comparison process by multiple times in the low-order field determining step. In the low-order field determining step, the low-order field computing section 20 sets bits from the first high-order bit to the eighth high-order bit to the data value (in the present example, 11010001) determined in the high-order field determining step, sets the ninth high-order bit to the comparison result by the corresponding comparing circuit 34, and supplies threshold data of which the tenth high-order bit is set to one to each of the 16 DACs 32.

In this way, the low-order field computing section 20 can respectively generate, from the 16 DACs 32, a boundary voltage located at ¼ or ¾ position when dividing, by four, a range between a threshold voltage corresponding to the maximum threshold data in which a comparison result showing that an analog input signal is not less than an analog value according to threshold data is generated in the high-order field determining step and a threshold voltage corresponding to the minimum threshold data in which a comparison result showing that the analog input signal is less than the analog value according to threshold data is generated in the high-order field determining step. The low-order field computing section 20 can generate a boundary voltage located at ¾ position to the DAC 32 in which the comparison result in the ninth high-order bit becomes High logic (one) and generate a boundary voltage located at ¼ position to the DAC 32 in which the comparison result in the ninth high-order bit becomes Low logic (zero).

The 16 comparing circuits 34 compare a threshold voltage and a voltage value $V_{IN}$ of the analog input signal, and each outputs a comparison result (i.e., a candidate value for the tenth bit). In the present example, three circuits of the 16 comparing circuits 34 output a comparison result (Low logic (zero)) showing that the analog input signal is not less than the analog value according to threshold data, and 13 circuits of the 16 comparing circuits 34 output a comparison result (High logic (one)) showing that the analog input signal is less than the analog value according to threshold data.

The low-order field determining section 22 adds the comparison results (i.e., candidate values for the tenth bit) output from the 16 comparing circuits 34. In the present example, the low-order field determining section 22 obtains 1101 as an added result because three Low logic (zero) and 13 High logic (one) are added.

Then, the low-order field determining section 22 adds a value (a value obtained by multiplying an addition value by two) obtained by shifting an addition value of the comparison results of the ninth bit in the left by one bit and an addition value of the comparison results of the tenth bit, and averages the added result with the number (16) of the comparing circuits 34. In other words, the low-order field determining section 22 computes a mean value for the plurality of candidate values of the low-order field (low-order two bits). Then, the low-order field determining section 22 determines the mean value as a data value of the low-order field. In the present example, the high-order field determining section 18 determines 01 as a data value from the ninth high-order bit to the tenth high-order bit.

As a result of the above process, the A-D converter 10 can output a ten-bit output value (in the present example, 1101000101). In addition, as an example, the low-order field determining section 22 may determine a value made by rounding off or cutting off a value after the decimal point in the mean value for the plurality of candidate values as a data value of the low-order field. Alternatively, the low-order field determining section 22 may determine a value after the decimal point of the mean value for the plurality of candidate values as a data value lower than this low-order field in the digital output signal.

Figure 10:
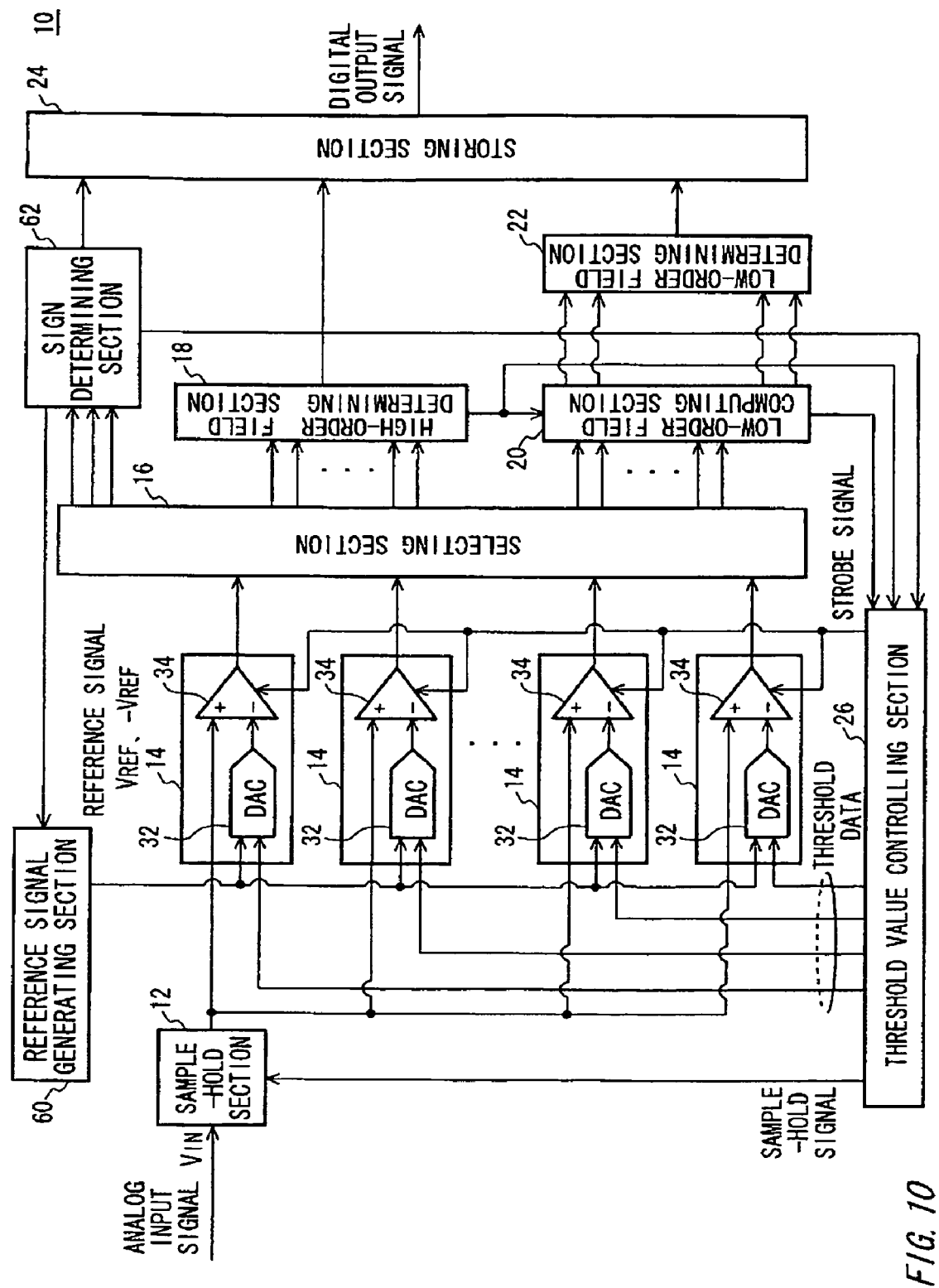
FIG. 10 is a view showing a configuration of an A-D converter according to an alternative example of the present embodiment.

FIG. 10 is a view showing a configuration of an A-D converter 10 according to an alternative example of the present embodiment. Since the A-D converter 10 according to an alternative example has the substantially same configuration and function as those of the A-D converter 10 according to the present embodiment shown in FIG. 1, the same components have the same reference number and their descriptions will be omitted.

The A-D converter 10 according to an alternative example further includes a reference signal generating section 60 and a sign determining section 62. The reference signal generating section 60 generates a reference signal to be supplied to the DAC 32 within the comparator 14. As an example, the reference signal generating section 60 may generate a plus-side reference signal ($V_{REF}$) and a minus-side reference signal ($-V_{REF}$).

The sign determining section 62 supplies threshold data designating an analog threshold value to zero to at least one of the plurality of comparators 14 in advance of the determination of a data value for a high-order field and a low-order field, in order to determine a sign of an analog input signal. As an example, the sign determining section 62 may compute a plurality of candidate values by concurrently executing a successive comparison process by multiple times, and determine a sign of an analog input signal based on the plurality of candidate values. More specifically, the sign determining section 62 may control the threshold value controlling section 26 to supply threshold data corresponding to ground potential to the plurality of comparators 14 and acquire a plurality of comparison results. Then, the sign determining section 62 may determine a sign of an analog input signal based on the plurality of comparison results. As an example, the low-order field determining section 22 may average the comparison results to determine the sign. In this way, according to the A-D converter 10 of an alternative example, it is possible to determine a sign with high precision.

Furthermore, as an example, the sign determining section 62 may generate a plus-side reference signal ($V_{REF}$) from the reference signal generating section 60 during determining a data value of a high-order field and a low-order field when the determined sign is plus, and generate a minus-side reference signal ($-V_{REF}$) from the reference signal generating section 60 during determining a data value of a high-order field and a low-order field when the determined sign is minus.

Furthermore, as an example, the sign determining section 62 may determine a data value by successive comparison by adding a field including the most significant bit except for a bit indicative of a sign to the bit indicative of a sign when the plus-side reference voltage ($V_{REF}$) and the minus-side reference voltage ($-V_{REF}$) are generated from the reference signal generating section 60. In this way, according to the A-D converter 10 of an alternative example, it is possible to efficiently perform a conversion process.

Figure 11:
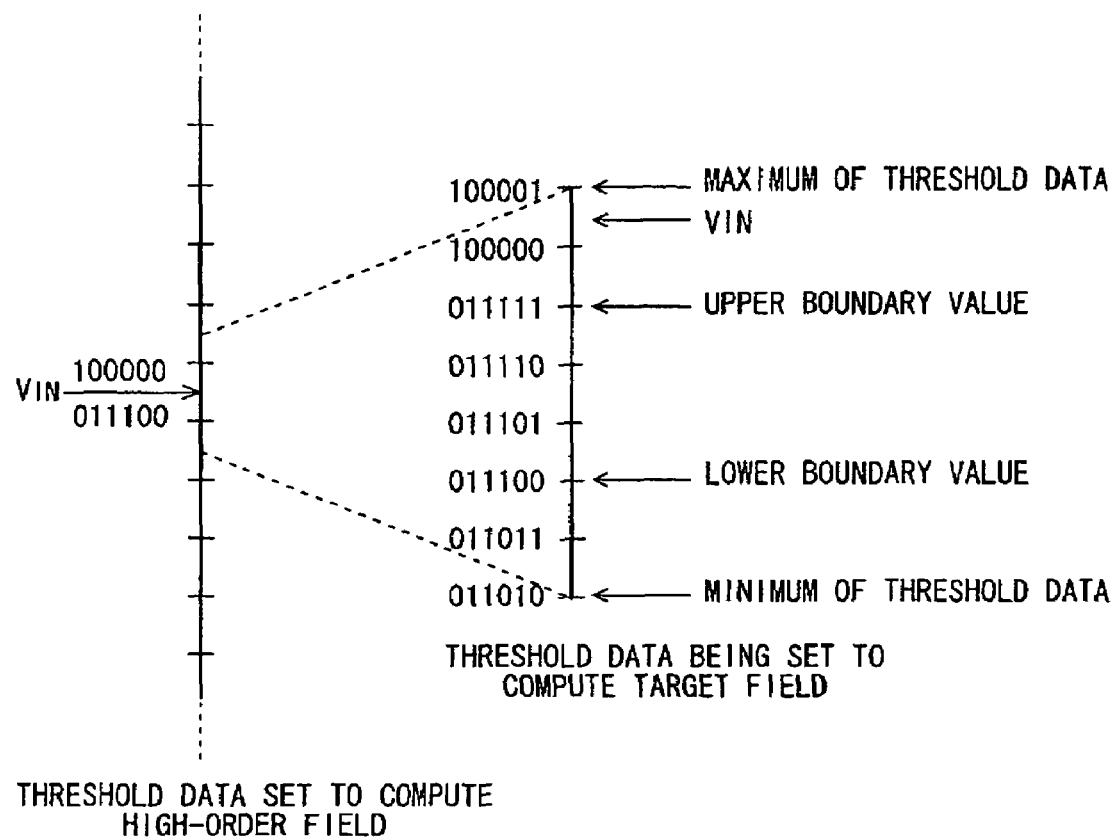
FIG. 11 is a view exemplary showing an overrange comparison process by a high-order field determining section and a low-order field computing section of an A-D converter according to an alternative example.

FIG. 11 is a view exemplary showing an overrange comparison process by a high-order field determining section 18 and a low-order field computing section 20 of an A-D converter 10 according to an alternative example. The high-order field determining section 18 may perform an overrange comparison process in a high-order determination phase after the second. Moreover, the low-order field computing section 20 may similarly perform an overrange comparison process.

When an overrange comparison process is performed, the high-order field determining section 18 and the low-order field computing section 20 set a maximum value of a plurality of threshold data to be supplied to the plurality of comparators 14 larger than an upper boundary value and set a minimum value of the plurality of threshold data to be supplied to the plurality of comparators 14 smaller than a lower boundary value.

Here, the upper boundary value is set to a data value in which a field upper than a field (a target field) of which a data value or a candidate value should be computed is already determined, and is digital output data in which a field value lower than the target field is set to a maximum value. In other words, the upper boundary value is digital output data set to a maximum value within a range of a data value (or a candidate value) narrowed down up to the just precedent phase. Moreover, the lower boundary value is set to a data value in which a field upper than a target field is already determined, and is digital output data in which a field value lower than the target field is set to a minimum value. In other words, the lower boundary value is digital output data set to a minimum value within a range of a data value (or a candidate value) narrowed down up to the just precedent phase.

For example, as shown in FIG. 11, when two bits of six bits are computed using an overrange comparison process and high-order four bits are determined to 0111, the upper boundary value is 011111 and the lower boundary value is 011100. Then, the high-order field determining section 18 and the low-order field computing section 20 may set a maximum value of the plurality of threshold data to be supplied to the plurality of comparators 14 to a value (in the present example, 100001) larger than the upper boundary value (011111) and set a minimum value of the plurality of threshold data to a value (in the present example, 011010) smaller than the lower boundary value (011100).

The plurality of comparators 14 compares an analog value according to such the plurality of threshold data and an analog input signal. Then, when a comparison result is that an analog input signal is not less than an analog value corresponding to threshold data larger than an upper boundary value, according to this comparison result, the high-order field determining section 18 and the low-order field computing section 20 compute a data value of a target field or a candidate value and also modify an already determined data value upper than this target field. Similarly, when a comparison result is that an analog input signal is less than an analog value corresponding to threshold data smaller than a lower boundary value, according to this comparison result, the high-order field determining section 18 and the low-order field computing section 20 compute a data value of a target field or a candidate value and also modify an already determined data value upper than this target field.

For example, although four bits of six bits are determined to 0111, when a comparison result is that an analog input signal is not less than an analog value corresponding to threshold data (e.g., 100000) larger than an upper boundary value, the high-order field determining section 18 and the low-order field computing section 20 may determine a low-order two-bit data value (e.g., zero) that becomes a target field as a comparison result and also modify the high-order four-bit data value already determined to a new value (e.g., 1000).

As described above, since the high-order field determining section 18 and the low-order field computing section 20 can modify an error produced in a high-order phase by performing an overrange comparison process, it is possible to output a digital output signal with high precision. In addition, the high-order field determining section 18 and the low-order field computing section 20 may increase a maximum value of the plurality of threshold data to be supplied to the plurality of comparators 14 larger than an upper boundary value and reduce a minimum value of the plurality of threshold data smaller than a lower boundary value. Moreover, the high-order field determining section 18 and the low-order field computing section 20 may reduce a minimum value of the plurality of threshold data smaller than a lower boundary value without increasing a maximum value of the plurality of threshold data to be supplied to the plurality of comparators 14 larger than an upper boundary value.

Figure 12:
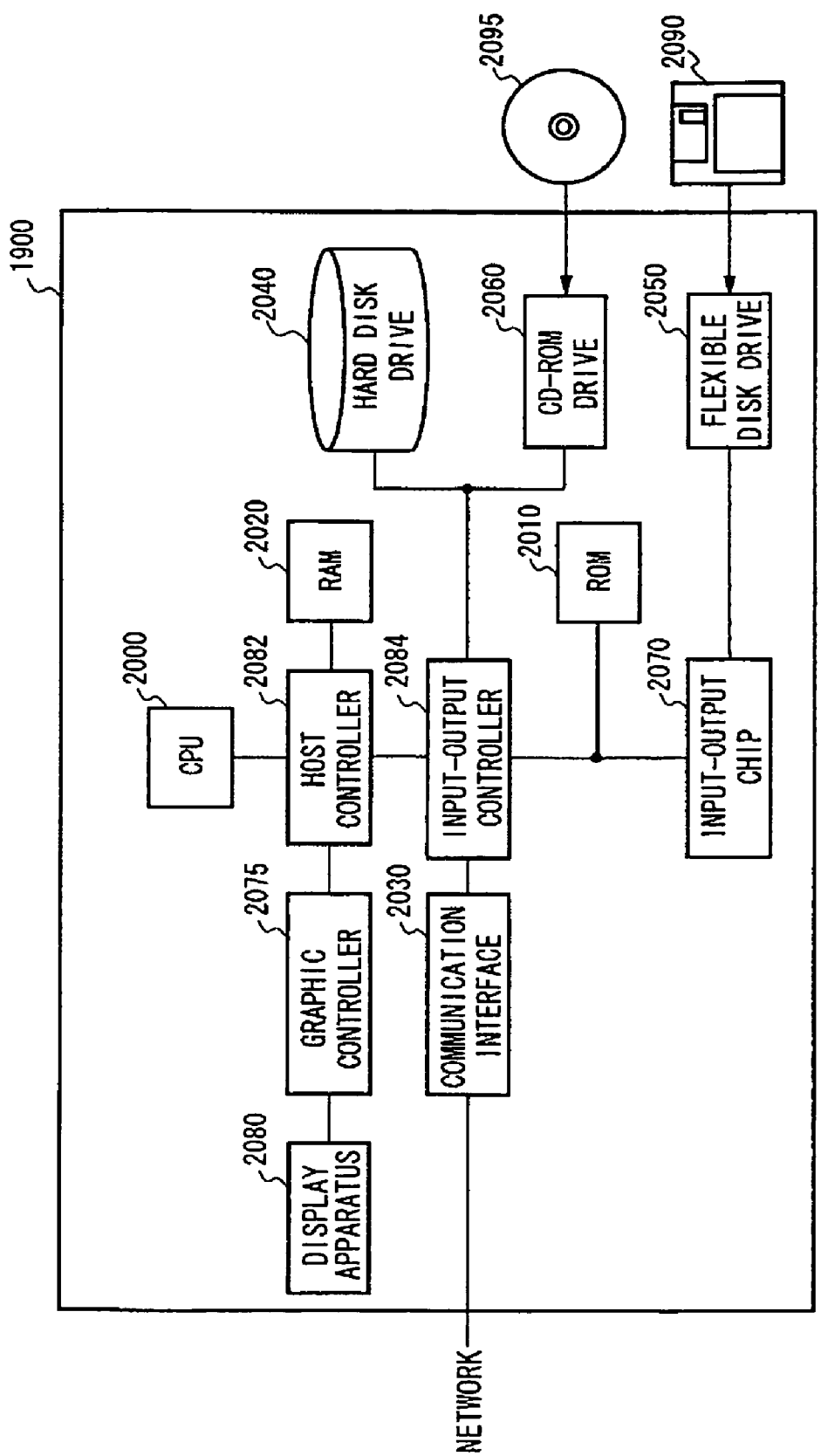
FIG. 12 is a view exemplary showing a hardware configuration of a computer according to an embodiment of the present invention.

FIG. 12 is a view exemplary showing a hardware configuration of a computer 1900 according to an embodiment of the present invention. The computer 1900 according to an embodiment of the present invention includes a CPU peripheral section, an input-output section, and a legacy input-output section. The CPU peripheral section has a CPU 2000, a RAM 2020, a graphic controller 2075, and a display apparatus 2080 that are interconnected by a host controller 2082. The input-output section has a communication interface 2030, a hard disk drive 2040, and a CD-ROM drive 2060 that are connected to the host controller 2082 by an input-output controller 2084. The legacy input-output section has a ROM 2010, a flexible disk drive 2050, and an input-output chip 2070 that are connected to the input-output controller 2084.

The host controller 2082 connects the RAM 2020 to the CPU 2000 and the graphic controller 2075 that access the RAM 2020 at high transfer rate. The CPU 2000 operates based on a program stored on the ROM 2010 and the RAM 2020, and controls each section. The graphic controller 2075 acquires image data to be generated by the CPU 2000 on a frame buffer provided in the RAM 2020, and displays the data on the display apparatus 2080. Alternatively, the graphic controller 2075 may include therein a frame buffer for storing image data generated from the CPU 2000.

The input-output controller 2084 connects the host controller 2082 to the communication interface 2030, the hard disk drive 2040, and the CD-ROM drive 2060 that are a comparatively fast input-output apparatus. The communication interface 2030 communicates with other apparatuses via network. The hard disk drive 2040 stores a program and data to be used by the CPU 2000 within the computer 1900. The CD-ROM drive 2060 reads a program or data from a CD-ROM 2095, and provides it to the hard disk drive 2040 via the RAM 2020.

Moreover, the ROM 2010 and the flexible disk drive 2050 and the input-output chip 2070 that are a comparatively low-speed input-output apparatus are connected to the input-output controller 2084. The ROM 2010 stores a boot program to be executed by the computer 1900 on starting and a program or the like dependent on hardware of the computer 1900. The flexible disk drive 2050 reads a program or data from a flexible disk 2090, and provides it to the hard disk drive 2040 via the RAM 2020. The input-output chip 2070 connects a various types of input-output apparatuses via the flexible disk drive 2050 and a parallel port, a serial port, a keyboard port, a mouse port, or the like.

A program provided to the hard disk drive 2040 via the RAM 2020 is stored on the flexible disk 2090, the CD-ROM 2095, or a recording medium such as an IC card, to be provided by a user. A program is read from a recording medium, is installed in the hard disk drive 2040 within the computer 1900 via the RAM 2020, and is executed in the CPU 2000.

A program that is installed in the computer 1900 and makes the computer 1900 function as a control apparatus for the A-D converter 10 includes a high-order field determining module, a low-order field computing module, a low-order field determining module, and a memory module. These program and modules work on the CPU 2000 or the like, and makes the computer 1900 respectively function as the high-order field determining section 18, the low-order field computing section 20, the low-order field determining section 22, and the storing section 24.

These program and modules described above may be stored on an outside recording medium. A recording medium can include an optical recording medium such as DVD and CD, a magneto-optical recording medium such as MO, a tape medium, a semiconductor memory such as an IC card in addition to the flexible disk 2090 and the CD-ROM 2095. Moreover, a storage device such as a hard disk or a RAM provided in a server system connected to a private communication network and Internet may be used as a recording medium, and a program may be provided to the computer 1900 via a network.

Although the present invention has been described by way of an exemplary embodiment, it should be understood that those skilled in the art might make many changes and substitutions without departing from the spirit and the scope of the present invention. It is obvious from the definition of the appended claims that embodiments with such modifications also belong to the scope of the present invention.

As apparent from the above descriptions, according to the present invention, it is possible to realize an A-D converter, an A-D convert method, and an A-D convert program for performing AD conversion with high precision by a small circuit scale and a fast operation.

What is claimed is:

1. An A-D converter that outputs a digital output signal obtained by digitalizing an analog input signal, comprising:
    a plurality of comparators that each compare the analog input signal and an analog threshold value according to designated digital threshold data;
    a high-order field determining section that narrows down a data value corresponding to a high-order field of a predetermined bit number in the digital output signal based on a plurality of comparison results obtained by supplying threshold data different from one another to the plurality of comparators;
    a low-order field computing section that computes a plurality of candidate values for a data value corresponding to a low-order field of a predetermined bit number located at a side lower than the high-order field by means of the plurality of comparators; and
    a low-order field determining section that determines a data value corresponding to the low-order field based on the plurality of candidate values.

2. The A-D converter as claimed in claim 1, wherein the low-order field computing section concurrently computes a candidate value for the data value corresponding to the low-order field by means of each of a plurality of groups obtained by dividing the plurality of comparators.

3. The A-D converter as claimed in claim 2, wherein the high-order field determining section
    concurrently supplies threshold data of which data values corresponding to the high-order field are different from one another to each of the plurality of comparators,
    performs at least one high-order determination phase in which the data value of the high-order field is narrowed down on a data value between the maximum threshold data by which a comparison result showing that the analog input signal is not less than an analog value according to this threshold data is generated and the minimum threshold data by which a comparison result showing that the analog input signal is less than the analog value according to this threshold data is generated, and
    determines the data value of the high-order field to one value.

4. The A-D converter as claimed in claim 3, wherein the low-order field computing section, for each of the plurality of groups obtained by dividing the plurality of comparators by one, sets an initial value of the candidate value to a data value determined by the high-order field determining section as a data value for the high-order field and zero as a data value for the low-order field, supplies the threshold data in which this bit in the candidate value is one to the comparator in this group sequentially from the most significant bit for each bit from the most significant bit to the least significant bit of the low-order field, updates the candidate value by setting this bit of the candidate value to one when the analog input signal is not less than the analog threshold value according to the threshold data and this bit of the candidate value to zero when the analog input signal is less than the analog threshold value, and supplies the candidate value obtained by updating the candidate value to the least significant bit of the low-order field to the low-order field determining section.

5. The A-D converter as claimed in claim 3, wherein the low-order field computing section, for each of the plurality of groups obtained by dividing the plurality of comparators into two or more comparators, concurrently supplies threshold data of which data values corresponding to the low-order field are different from one another to each of the plurality of comparators, performs at least one low-order determination phase in which a candidate value of the data value of the low-order field is narrowed down on a data value between the maximum threshold data by which a comparison result showing that the analog input signal is not less than an analog value according to this threshold data is generated and the minimum threshold data by which a comparison result showing that the analog input signal is less than the analog value according to this threshold data is generated, in order to narrow down a data value of the low-order field of the digital output signal, and determines the data value of the low-order field to one value.

6. The A-D converter as claimed in claim 1, wherein the low-order field computing section performs, for each of the plurality of candidate values, at least one low-order determination phase in which a data value corresponding to the low-order field is narrowed down and determines the data value of the low-order field of this candidate value to one value, based on a plurality of comparison results obtained by supplying threshold data different from one another to the plurality of comparators.

7. The A-D converter as claimed in claim 2, wherein the low-order field determining section determines a mean value for the plurality of candidate values as the data value of the low-order field.

8. The A-D converter as claimed in claim 7, wherein the low-order field determining section determines, among the plurality of candidate values, a mean value for at least one candidate value as the data value of the low-order field, the difference between the mean value for at least one candidate value and the mean value for the plurality of candidate values being not more than a predetermined maximum error value.

9. The A-D converter as claimed in claim 1, further comprising a sign determining section that supplies the threshold data in which an analog threshold value zero is designated to at least one of the plurality of comparators and determines a sign of the analog input signal in advance of the determination of data values for the high-order field and the low-order field.

10. An A-D convert method for outputting a digital output signal obtained by digitalizing an analog input signal, comprising:

a high-order field determining step of narrowing down a data value corresponding to a high-order field of a predetermined bit number in the digital output signal based on a plurality of comparison results obtained by supplying threshold data different from one another to a plurality of comparators that each compare the analog input signal and an analog threshold value according to designated digital threshold data;

a low-order field computing step of computing a plurality of candidate values for a data value corresponding to a low-order field of a predetermined bit number located at a side lower than the high-order field by means of the plurality of comparators; and a low-order field determining step of determining a data value corresponding to the low-order field based on the plurality of candidate values.

11. An A-D convert computer program product having computer instructions, recorded on a computer readable medium for outputting a digital output signal obtained by digitalizing an analog input signal by means of a computer, the program for enabling a computer executing the computer instructions to perform operations comprising:

narrowing down a data value corresponding to a high-order field of a predetermined bit number in the digital output signal based on a plurality of comparison results obtained by supplying threshold data different from one another to a plurality of comparators that each compare the analog input signal and an analog threshold value according to designated digital threshold data;

computing a plurality of candidate values for a data value corresponding to a low-order field of a predetermined bit number located at a side lower than the high-order field by means of the plurality of comparators;

determining a data value corresponding to the low-order field based on the plurality of candidate values; and outputting the digital output signal having the data value.

12. The A-D converter as claimed in claim 6, wherein the low-order field determining section determines a mean value for the plurality of candidate values as the data value of the low-order field.

* * * * *